US009732052B2

(12) United States Patent
Tachdjian et al.

(10) Patent No.: US 9,732,052 B2
(45) Date of Patent: *Aug. 15, 2017

(54) PROCESSES AND INTERMEDIATES FOR MAKING SWEET TASTE ENHANCERS

(71) Applicant: Senomyx, Inc., San Diego, CA (US)

(72) Inventors: Catherine Tachdjian, San Diego, CA (US); Donald S. Karanewsky, Escondido, CA (US); Xiao-Qing Tang, Holmdel, NJ (US); Qing Chen, San Diego, CA (US); Peter Leeming, Monrovia, CA (US); Tayyab Rashid, Rancho Cucamonga, CA (US); Daniel Levin, La Canada, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,894

(22) Filed: Jun. 16, 2016

(65) Prior Publication Data

US 2016/0289200 A1 Oct. 6, 2016

Related U.S. Application Data

(62) Division of application No. 14/053,897, filed on Oct. 15, 2013, now Pat. No. 9,382,196, which is a division of application No. 13/056,843, filed as application No. PCT/US2009/052048 on Jul. 29, 2009, now Pat. No. 8,586,733.

(60) Provisional application No. 61/085,206, filed on Jul. 31, 2008, provisional application No. 61/167,654, filed on Apr. 8, 2009.

(51) Int. Cl.
| | |
|---|---|
| *C07D 285/16* | (2006.01) |
| *C01B 21/096* | (2006.01) |
| *C07C 235/20* | (2006.01) |
| *C07C 237/44* | (2006.01) |
| *C07C 255/54* | (2006.01) |
| *C07C 255/59* | (2006.01) |
| *C07C 307/10* | (2006.01) |
| *C07C 231/02* | (2006.01) |
| *C07C 231/14* | (2006.01) |
| *C07C 253/30* | (2006.01) |
| *C07C 255/57* | (2006.01) |
| *C07C 303/40* | (2006.01) |

(52) U.S. Cl.
CPC .......... *C07D 285/16* (2013.01); *C01B 21/096* (2013.01); *C07C 231/02* (2013.01); *C07C 231/14* (2013.01); *C07C 235/20* (2013.01); *C07C 237/44* (2013.01); *C07C 253/30* (2013.01); *C07C 255/54* (2013.01); *C07C 255/57* (2013.01); *C07C 255/59* (2013.01); *C07C 303/40* (2013.01); *C07C 307/10* (2013.01)

(58) Field of Classification Search
CPC .................................................... C07D 285/16
USPC .......................................................... 558/414
See application file for complete search history.

(56) References Cited

U.S. PATENT DOCUMENTS

| | | | |
|---|---|---|---|
| 3,278,532 A | 10/1966 | Houlihan | |
| 3,843,804 A | 10/1974 | Evers et al. | |
| 3,845,770 A | 11/1974 | Theeuwes et al. | |
| 3,857,972 A | 12/1974 | Evers et al. | |
| 3,916,899 A | 11/1975 | Theeuwes et al. | |
| 3,957,783 A | 5/1976 | Hirohashi et al. | |
| 3,960,860 A | 6/1976 | Katz et al. | |
| 3,966,965 A | 6/1976 | Sellstedt et al. | |
| 4,036,837 A | 7/1977 | Sellstedt et al. | |
| 4,137,325 A | 1/1979 | Sellstedt et al. | |
| 4,146,716 A | 3/1979 | Cox et al. | |
| 4,196,207 A | 4/1980 | Webber et al. | |
| 4,377,580 A | 3/1983 | Ueda et al. | |
| 4,765,539 A | 8/1988 | Noakes et al. | |
| 4,960,870 A | 10/1990 | Lehmann | |
| 5,112,598 A | 5/1992 | Biesalski | |

(Continued)

FOREIGN PATENT DOCUMENTS

| | | |
|---|---|---|
| CA | 2879661 A1 | 2/2014 |
| CN | 1033624 | 7/1989 |

(Continued)

OTHER PUBLICATIONS

Abdel-Megied et al., 1998, Synthesis of 5,6-dihydronaphtho[1',2':4,5]thieno[2,3-d]pyrimidines, 5,6-dihydronaphtho[1',2':4,5]thieno[3,2-e] [1,2,4] triazolo[1,5-c]pyrimidines, and some of their nucleosides, Sulfur Letters, 21(6):269-284.

(Continued)

*Primary Examiner* — Kahsay Habte
(74) *Attorney, Agent, or Firm* — Knobbe Martens Olson & Bear, LLP

(57) ABSTRACT

The present invention includes methods/processes and intermediates for preparing compounds having structural Formula (I):

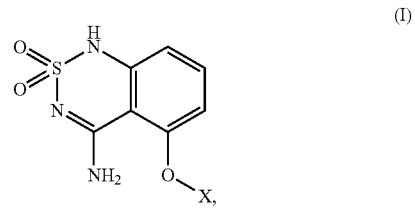

wherein X is alkyl, substituted alkyl, alkenyl, substituted alkenyl, heteroalkyl, substituted heteroalkyl, heteroalkenyl, or substituted heteroalkenyl.

11 Claims, No Drawings

(56) References Cited

U.S. PATENT DOCUMENTS

| | | | |
|---|---|---|---|
| 5,192,785 A | 3/1993 | Lo et al. | |
| 5,380,541 A | 1/1995 | Beyts et al. | |
| 5,504,095 A | 4/1996 | Nakane et al. | |
| 5,556,611 A | 9/1996 | Biesalski | |
| 5,698,155 A | 12/1997 | Grosswald et al. | |
| 5,801,180 A | 9/1998 | Takase et al. | |
| 5,950,619 A | 9/1999 | van der Linden et al. | |
| 5,954,047 A | 9/1999 | Armer et al. | |
| 5,970,974 A | 10/1999 | van der Linden et al. | |
| 5,990,117 A | 11/1999 | Pamukcu et al. | |
| 6,046,206 A | 4/2000 | Pamukcu et al. | |
| 6,110,920 A | 8/2000 | Rochus et al. | |
| 6,316,454 B1 | 11/2001 | Uckun et al. | |
| 6,316,565 B1 | 11/2001 | Jung et al. | |
| 6,475,544 B1 | 11/2002 | Hiramoto et al. | |
| 6,852,862 B2 | 2/2005 | Nishizawa et al. | |
| 7,105,650 B2 | 9/2006 | Adler | |
| 7,476,399 B2 | 1/2009 | Tachdjian et al. | |
| 7,915,410 B2 | 3/2011 | Johnson et al. | |
| 7,928,111 B2 | 4/2011 | Tachdjian et al. | |
| 8,541,421 B2 | 9/2013 | Tachdjian et al. | |
| 8,586,733 B2 * | 11/2013 | Tachdjian | C01B 21/096 544/11 |
| 8,633,186 B2 | 1/2014 | Tachdjian et al. | |
| 8,968,708 B2 | 3/2015 | Tachdjian et al. | |
| 8,968,709 B2 | 3/2015 | Yang et al. | |
| 9,000,054 B2 | 4/2015 | Tachdjian et al. | |
| 9,000,151 B2 | 4/2015 | Adamski-Werner et al. | |
| 9,138,013 B2 | 9/2015 | Tachdjian et al. | |
| 9,181,276 B2 | 11/2015 | Tachdjian et al. | |
| 9,371,317 B2 | 6/2016 | Adamski-Werner et al. | |
| 9,382,196 B2 * | 7/2016 | Tachdjian | C01B 21/096 |
| 9,420,814 B2 | 8/2016 | Tachdjian et al. | |
| 9,475,803 B2 | 10/2016 | Adamski-Werner et al. | |
| 2002/0025366 A1 | 2/2002 | Jager et al. | |
| 2003/0008344 A1 | 1/2003 | Adler et al. | |
| 2003/0054448 A1 | 3/2003 | Adler et al. | |
| 2003/0232407 A1 | 12/2003 | Zoller et al. | |
| 2004/0127435 A1 | 7/2004 | Carson et al. | |
| 2004/0197453 A1 | 10/2004 | Hirao et al. | |
| 2005/0032158 A1 | 2/2005 | Adler et al. | |
| 2005/0084506 A1 | 4/2005 | Tachdjian et al. | |
| 2005/0196503 A1 | 9/2005 | Srivastava | |
| 2006/0045953 A1 | 3/2006 | Tachdjian et al. | |
| 2006/0083695 A1 | 4/2006 | Mori | |
| 2006/0134693 A1 | 6/2006 | Servant et al. | |
| 2006/0135552 A1 | 6/2006 | Malherbe et al. | |
| 2006/0257543 A1 | 11/2006 | Tachdjian et al. | |
| 2006/0257550 A1 | 11/2006 | Mori | |
| 2006/0270668 A1 | 11/2006 | Chew et al. | |
| 2007/0003680 A1 | 1/2007 | Tachdjian et al. | |
| 2007/0010480 A1 | 1/2007 | Rusing et al. | |
| 2007/0104701 A1 | 5/2007 | Ueda et al. | |
| 2007/0104709 A1 | 5/2007 | Li et al. | |
| 2008/0249189 A1 | 10/2008 | Atwal | |
| 2008/0306053 A1 | 12/2008 | Tachdjian et al. | |
| 2008/0306093 A1 | 12/2008 | Servant et al. | |
| 2009/0286863 A1 | 11/2009 | Bruge et al. | |
| 2011/0195170 A1 | 8/2011 | Shigemura et al. | |
| 2011/0224155 A1 | 9/2011 | Tachdjian et al. | |
| 2011/0230502 A1 | 9/2011 | Tachdjian et al. | |
| 2011/0245353 A1 | 10/2011 | Tachdjian et al. | |
| 2012/0041078 A1 | 2/2012 | Tachdjian et al. | |
| 2014/0094453 A1 | 4/2014 | Tachdjian et al. | |
| 2015/0257422 A1 | 9/2015 | Adamski-Werner et al. | |
| 2015/0374020 A1 | 12/2015 | Tachdjian et al. | |
| 2015/0376176 A1 | 12/2015 | Adamski-Werner et al. | |
| 2016/0331013 A1 | 11/2016 | Tachdjian et al. | |
| 2017/0029416 A1 | 2/2017 | Adamski-Werner et al. | |

FOREIGN PATENT DOCUMENTS

| | | |
|---|---|---|
| CN | 101035442 | 9/2007 |
| CN | 101505601 | 8/2009 |
| DE | 22 58 403 | 6/1973 |
| EP | 0 227 450 | 7/1987 |
| EP | 0 530 994 | 3/1993 |
| EP | 0 584 797 | 3/1994 |
| EP | 0 887 344 | 12/1998 |
| ES | 0472163 | 3/1979 |
| ES | 8507558 | 12/1985 |
| GB | 951651 | 3/1964 |
| JP | 59-051290 | 3/1984 |
| JP | 63-87959 | 4/1988 |
| JP | 02-238856 | 9/1990 |
| WO | WO 89/00563 | 1/1989 |
| WO | WO 93/13104 | 7/1993 |
| WO | WO 98/06722 | 2/1998 |
| WO | WO 00/28952 | 5/2000 |
| WO | WO 00/71524 | 11/2000 |
| WO | WO 01/04086 | 1/2001 |
| WO | WO 03/001876 | 1/2003 |
| WO | WO 03/004992 | 1/2003 |
| WO | WO 03/007734 | 1/2003 |
| WO | WO 03/022214 | 3/2003 |
| WO | WO 03/051878 | 6/2003 |
| WO | WO 03/055866 | 7/2003 |
| WO | WO 03/076427 | 9/2003 |
| WO | WO 2004/056365 | 7/2004 |
| WO | WO 2005/015158 | 2/2005 |
| WO | WO 2005/016889 | 2/2005 |
| WO | WO 2005/116069 | 12/2005 |
| WO | WO 2005/123724 | 12/2005 |
| WO | WO 2006/076102 | 7/2006 |
| WO | WO 2006/084184 | 8/2006 |
| WO | WO 2006/113422 | 10/2006 |
| WO | WO 2006/113432 | 10/2006 |
| WO | WO 2007/004709 | 1/2007 |
| WO | WO 2007/047988 | 4/2007 |
| WO | WO 2007/071963 | 6/2007 |
| WO | WO 2008/003378 | 1/2008 |
| WO | WO 2008/154221 | 12/2008 |
| WO | WO 2012/001547 | 1/2012 |
| WO | WO 2012/054526 | 4/2012 |
| WO | WO 2014/023583 | 2/2014 |
| WO | WO 2014/140864 | 9/2014 |

OTHER PUBLICATIONS

Abdelrazek et al., 1992, Heterocyclic synthesis with nitriles: synthesis of some novel thiophene and thieno[2,3-d]pyrimidine derivatives, Phosphorus, Sulfur and Silicon and the Related Elements, 72(1-4):93-97.

Albrecht et al., 1979, Synthesis of 1,2,6-Thiadiazine 1,1-Dioxides via Isoxazolylsulfamides, J. Org. Chem. 44:4191-4194.

Alderman, 1984, A Review of Cellulose Ethers in Hydrophilic Matrices for Oral Controlled-Release Dosage Forms, Int. J. Pharm. Tech. & Prod. Mfr. 5(3):1-9.

Bamba et al., 1979, Release mechanisms in Gelforming Sustained Release Preparations, Int. J. Pharm. 2:307-315.

Bancroft, 1978, Synthesis and Reduction of some 1H-2,1,3-Benzothiadiazin-4(3H)one 2,2-Dioxides, J. Heterocyclic Chem., 15:1521-1523.

Bandurco et al., 1987, Synthesis and cardiotonic activity of a series of substituted 4-alkyl-2(1H)-quinazolinones 1421, J. Med. Chem, 30:1421-1426.

Belikov, 1993, Pharmaceutical Chemistry, High School, vol. 1, pp. 43-47.

Bellur et al., 2006, Synthesis of 4-(3-hydroxyalkyl)pyrimidines by ring transformation reactions of 2-alkylidenetetrahydrofurans with amidines, Tetrahedron 62:5426-5434.

Berge et al., 1977, Pharmaceutical Salts, J. Pharm. Sci. 66(1):1-19.

Bhattacharya et al., 1994, Thieno[3',2':4,5][1]benzothieno [2,3-d]pyrimidine derivatives: synthesis and conformation, Journal of the Chemical Society, Perkin Transactions 1: Organic and Bio-Organic Chemistry, 6:689-693.

Blackburn et al., 2006, Identification and characterization of aminopiperidinequinolones and quinazolinones as MCHr1 antagonists, Bioorg. & Med. Chem. Lett. 16:2621-2627.

(56) References Cited

OTHER PUBLICATIONS

Blanksma, 1908, Bereiding der oxymethyl (oxyethyl) cyaan-nitrobenzolen, Chemisch Weekblad, 5(44):789-795.
Boarland et al., 1951, Monosubstituted Pyrimidines, and the Action of Thiourea on Chloropyrimidines, J. Chem. Soc. 1218-1221.
Brodsky et al., 2005, Oxaziridine-mediated catalytic hydroxylation of unactivated 3° C-H bonds using hydrogen peroxide, J. Am. Chem. Soc., 127:15391-15393, and Supporting Material (16 pp.).
Brown, et al., 1990, Evolution of a Series of Peptidoleukotriene Antagonists: Synthesis and Structure-Activity Relationships of 1,6-Disubstituted Indoles and Indazoles, J. Med. Chem. 33:1771-1781.
Buck et al., 1991, A Novel Multigene Family May Encode Odorant Receptors: A Molecular Basis for Odor Recognition, Cell 65(1):175-187.
Calkins, May 2010, 2,1-Benzothiazines: Preparation and Reactivity, PhD thesis, University of Missouri-Columbia, https://mospace.umsystem.edu/xmlui/handle/10355/830; 290 pp.
Campillo et al., 1998, A Novel Tetracyclic System Containing the 1,2,6-Thiadiazine Ring: Synthesis, Structural Assignment and Tautomeric Studies, Heterocycles, 48(3):1833-1840.
Campillo et al., 2004, A study of peculiar tautomerism of pyrido[2,3-c][1,2,6]thiadiazine 2,2-dioxide system, J. Mol. Struct. 678:83-89.
Chandrashekar et al., 2000, T2R5 Function as Bitter Taste Receptors, Cell 100:703-711.
Chemical Abstracts Service, Registry No. 501002-78-4, Entered STN Mar. 31, 2003.
Cheng et al., 1958, Potential Purine Antagonists. XII. Synthesis of 1-Alkyl(aryl)-4,6-disubstituted Pyrazolo [3,4-d] pyrimidines, J. Org. Chem. 23:852-861.
Chien et al., 2004, Nucleosides XI. Synthesis and Antiviral Evaluation of 5'-Alkylthio-5'-deoxy Quinazolinone Nucleoside Derivatives as S-Adenosyl-L-homocysteine Analogs, Chem. Pharm. Bull. 52(12):1422-1426.
Clauss et al., 1970, Cycloadditionen von Halogensulfonylisocyanaten an Acetylene, Tetrahedron Lett. 2:119-122.
Corbett et al., 2000, Novel 2,2-Dioxide-4,4-disubstituted-1,3-H-2,1,3-benzothiadiazines as Non-Nucleside Reverse Transcriptase Inhibitors, Bioorg. Med. Chem. Lett. 10:193-195.
Da Settimo et al., 2005, Naphtho[1,2-d]isothiazole Acetic Acid Derivatives as a Novel Class of Selective Aldose Reductase Inhibitors, J. Med. Chem. 48:6897-6907.
Dominguez et al., 2000, Efficient synthesis of 4,4-disubstituted-3,4-dihydro-1H-2,1,3-benzothiadiazine 2,2-dioxides, Tetrahedron Lett. 41:9825-9828.
Dorwald, 2005, Side Reactions in Organic Synthesis: A Guide to Successful Synthesis Design, Weinheim: Wiley-VCH Verlag GmbH & Co. KGaA, Preface.
Doucet-Personeni et al., 2001, A Structure-Based Design Approach to the Development of Novel, Reversible AChE Inhibitors, J. Med. Chem., 44:3203-3215.
During et al., 1989, Controlled Release of Dopamine from a Polymeric Brain Implant: In Vivo Characterization, Ann. Neurol. 25:351-356.
Elmegeed et al., 2005, Novel synthesizes aminosteroidal heterocycles intervention for inhibiting iron-induced induced oxidative stress, Eur. J. Med. Chem. 40:1283-1294.
El-Sherbeny et al., 2000, Novel Pyridothienopyrimidine and Pyridothienothiazine Derivatives as Potential Antiviral and Antitumor Agents, Med. Chem. Res. 10:122-135.
Etter et al., 1986, An Enolized Sulfonamide Formed by Strong Hydrogen Bonding to Triphenylphosphine Oxide, J. Org. Chem. 51:5405-5408.
Fan et al., 2004, Transient Silylation of the Guanosine O6 and Amino Groups Facilitates N-Acylation, Org. Lett. 6(15):2555-2557.
Francis et al., 1991, Anxiolytic Properties of Certain Annelated [1,2,4]Triazolo[1,5-c]pyrimidin-5(6H)-ones, J. Med. Chem. 34:2899-2906.

Frauli et al., 2006, Amino-pyrrolidine tricarboxylic acids give new insight into group III metabotropic glutamate receptor activation mechanism, Molecular Pharmacology, 72(3):704-712.
Freidlander, et al., 1912, Uber brom- and methoxyderivate des indigos, Justus Liebigs Annalen der Chemie, 388:23-49.
Fuentes-Cabrera et al., 2005, Size-expanded DNA bases: an ab initio study of their structural and electronic properties, Journal of Physical Chemistry B, 109(44):21135-21139.
Garcia-Munoz et al., 1976, Synthesis of Purine-Like Ring Systems Derived From 1,2,6-Thiadiazine 1,1-Dioxide, J. Heterocyclic Chem. 13:793-796.
Goya et al., 1984, Fused 1,2,6-Thiadiazines: Tetrahydrobenzo[b]thieno[2,3-c] [1,2,6]thiadiazine 2,2-Dioxides, Arch. Pharm. (Weinheim) 317:777-781.
Goya et al., 1985, Fused thiadiazines, CAPLUS Accession No. 1987:18628, 2 pages, abstract of ES 531159 A1.
Goya et al., 1986, Aminopyrido [2,3-c] [1,2,6] Thiadiazine 2,2-Dioxides: Synthesis and Physico-chemical Properties, Chemica Scripta, 26:607-611.
Goya et al., 1986, N-Glucosyl-5-Amino-4-Carbamoyl- and 4-Ethoxycarbonylimidazoles as Potential Precursors of 4-Oxoimidazo[4,5-c]-1,2,6-thiadiazine 2,2-Dioxides, Heterocycles 24:3451-3458.
Goya et al., 1987, Synthesis of 2S-Dioxo Isosteres of Purine and Pyrimidine Nucleosides IV. Selective Glycosylation of 4-Amino-5H-Imidazo [4,5-c] -1,2,6-Thiadiazine 2,2-Dioxide, Nucleosides & Nucleotides, 6(3), 631-642.
Goya et al., 1988, Pteridine Analogues; Synthesis and Physico-Chemical Properties of 7-Oxopyrazino [2,3-c][1,2,6] thiadiazine 2,2-Dioxides, Liebigs Ann. Chem., 121-124.
Goya et al., 1988, Synthesis and Cytostatic Screening of an $SO_2$ Analogue of Doridosine, Arch. Pharm. (Weinheim), 321:99-101.
Guedira et al., 1992, Ambident behavior of ketone enolate anions in $S_NAr$ substitutions on fluorobenzonitriel substrates, J. Org. Chem. 57:5577-5585, and Supporting Material.
Harris et al., 1990, Antifolate and Antibacterial Activities of 5-Substituted 2,4- diaminoquinazolines, J. Med. Chem. 33(1):434-444.
Hauser et al., 1953, Synthesis of 5-Phenyl-4,6-Dimethyl-2-Pyrimidol and Derivatives from the Cyclization of Urea with 3-Phenyl-2,4-Pentanedione, J. Org. Chem. 18:588-593.
Hirayama et al., 2002, The Discovery of YM-60828: A Potent, Selective and Orally-Bioavailable Factor Xa Inhibito, Bioorg. & Med. Chem. 10:1509-1523.
Hirohashi et al., 1975, Nuclear Magnetic Resonance Studies of Bicyclic Thiophene Derivatives. I. Ring Current Effects of the Benzene Ring on the $H_\alpha$ and $H_\beta$ signals of the Thiophene Ring in Benzoylthiophene, Thienopyrimidine, and Thienodiazepine Derivatives, Bull. Chem. Soc. Jpn., 48(1):147-156.
Hirota et al., 2003, Synthesis and Biological Evaluation of 2,8-Disubstituted 9-Benzyladenines: Discovery of 8-Mercaptoadenines as Potent Interferon-Inducers, Bioorg. Med. Chem. 11:2715-2722.
Hoon et al., 1991, Putative Mammalian Taste Receptors: A Class of Taste-Specific GPCRs with Distinct Topographic Selectivity. Cell 96:541-551.
Howard et al., 1989, Intracerebral drug delivery in rats with lesion-induced memory deficits, J. Neurosurg. 71:105-112.
Hu et al., 2004, Organic Reactions in Ionic Liquids: Gewald Synthesis of 2-Aminothiophenes Catalyzed by Ethylenediammonium Diacetate, Synth Commun. 34(20):3801-3806.
Jordan, 2003, Tamoxifen: A Most Unlikely Pioneering Medicine, Nature Reviews: Drug Discovery 2003, 2:205-213.
Jung et al., 2006, Discovery of Novel and Potent thiazoloquinazolines as Selective Aurora A and B Kinase Inhibitors, J. Med. Chem. 49:955-970.
Justoni et al., 1951, Studi su sostanze a presumibile azione chemioterapica antitubercolare, Il Farmaco, 6:849-858.
Kamal et al., Cyclization of 2-(Carbamoyloxy)- and 2-(Sulfamoyloxy)benzoates Mediated by Liver Microsomes, J. Org. Chem. 53:4112-4114.
Kamal et al., 1989, Enzymatic Cyclization of 2-(Carbamoyloxy)Benzoates, 2-(Sulfamoyloxy)-Benzoates and 2-(Carbamoyloxy)benzopenones with Yeast and Lipase, Heterocycles 29:1391-1397.

(56) References Cited

OTHER PUBLICATIONS

Kanbe et al., 2006, Discovery of thiochroman derivatives bearing a carboxy-containing side chain as orally active pure antiestrogens, Bioorg. & Med. Chem. Lett. 16:4090-4094.
Kanuma et al., 2005, Lead optimization of 4-(dimethylamino)quinazolines, potent and selective antagonists for the melanin-concentrating hormone receptor 1, Bioorg. & Med. Chem. Lett. 15(17):3853-3856.
Khabnadideh et al., 2005, Design, synthesis and evaluation of 2,4-diaminoquinazolines as inhibitors of trypanosomal and leishmanial dihydrofolate reductase, Bioorg. Med. Chem. 13:2637-2649.
Khatoon et al., 2004, Pyrido [2,3-d]pyrimidines and their ribofuranosides: synthesis and antimicrobial evaluations, Indian Journal of Heterocyclic Chemistry, 13(4):331-334.
Klaubert et al., 1981, N-(Aminophenyl)oxamic acids and esters as potent, orally active antiallergy agents, J. Med. Chem. 24(6):742-748.
Klinger et al., 2006, Inhibition of Carbonic Anhydrase-II by Sulfamate and Sulfamide Groups: An Investigation Involving Direct Thermodynamic Binding Measurements, J. Med. Chem. 49(12):3496-3500.
Kokrashvili et al., 2009, Taste signaling elements expressed in gut enteroendocrine cells regulate nutrient-responsive secretion of gut hormones, Am. J. Clin Nutr, 90(suppl):1S-4S.
Kyriazis et al., 2012, Sweet taste receptor signaling in beta cells mediates fructose-induced potentation of glucose-stimulated insulin secretion, PNAS Early Edition, 9 pp.
Kyte et al., 1982, A Simple Method for Displaying the Hydropathic Character of a Protein, J. Mol. Biol. 157:105-132.
Langer et al., 1983, Chemical and Physical Structure of Polymers as Carriers for Controlled Release of Bioactive Agents: A Review, J. Macromol. Sci. Rev. Macromol Chem. 23:61-126.
Langer, 1990, New Methods of Drug Delivery, Science 249:1527-1533.
Lee et al., 2006, Acetonitrile-Mediated Synthesis of 2,4-Dichloroquinoline from 2-Ethynyl-aniline and 2,4-Dichloroquinazoline from Anthranilonitrile, Synlett, 2006 No. 1:65-68.
Leistner et al., 1989, Polycyclic azines with heteroatoms in the 1- and 3-positions, Part 22. A facile synthesis of 2-(alkylthio)-4-aminothieno[2,3-d]pyrimidi nes, Archiv. der Pharmazie (Weinheim, Germany), 322(4):227-230.
Levy et al., 1985, Inhibition of Calcification of Bioprosthetic Heart Valves by Local Controlled-Release Diphosphonate, Science 228:190-192.
Li et al., 1997, Preformulation studies for the development of a parenteral liquid formulation of an antitumor agent, AG337, PDA Journal of Pharmaceutical Science and Technology, 51(5):181-186.
Li et al., 2002, Human receptors for sweet and umami taste, Proc. Natl. Acad. Sci. USA 99:4692-4696.
Linkies et al., 1990, Ein neues Verfahren zur Herstellung von 6-Methyl-1,2,3-oxathiazin-4(3H)-on-2,2-dioxid Kaliumsalz (Acesulfam-K), Synthesis 405-406.
Liu et al., 2007, Discovery of a new class of 4-anilinopyrimidines as potent c-Jun N-terminal kinase inhibitors: Synthesis and SAR studies, Bioorg. & Med. Chem. Lett. 17:668-672.
Martinez et al., 2000, Benzothiadiazine Dioxide Dibenzyl Derivatives as Potent Human Cytomegalovirus Inhibitors: Synthesis and Comparative Molecular Field Analysis, J. Med. Chem. 43(17):3218-3225.
Meyer et al., 1979, Synthesis of fused [1,2,6]thiadiazine 1,1-dioxides as potential transition-state analogue inhibitors of xanthine oxidase and guanase, J. Med. Chem. 22(8):944-948.
Naganawa et al., 2006, Further optimization of sulfonamide analogs as EP1 receptor antagonists: Synthesis and evaluation of bioisosteres for the carboxylic acid group, Bioorg. Med. Chem. 14:7121-7137.

Nie et al., 2005, Distinct Contributions of T1 R2 and T1R3 Taste Receptor Subunits to the Detection of Sweet Stimuli, Curr. Biol. 15(21):1948-1952.
Pal et al., 2005, Synthesis and Cyclooxygenase-2 (COX-2) Inhibiting Properties of 1,5-Diarylpyrazoles Possessing N-Substitution on the Sulfonamide ($-SO_2NH_2$) Moiety, Letters in Drug Design & Discovery 2:329-340.
Patil, 1980, The synthesis of thieno[2,3-d]pyrimidine nucleosides related to the naturally occurring nucleosides cytidine and uridine, Journal of the Chemical Society, Perkin Transactions 1: Organic and Bio-Organic Chemistry, 9:1853-1858.
Petersen et al., 1996, Synthesis of heterocycles containing two cytosine or two guanine base-pairing sites: novel tectons for self-assembly, Bioorg. & Med. Chem. 4(7):1107-1112.
PubChemCompound, datasheets, retrieved from internet: CID Nos. 12715714 (Feb. 8, 2007), 12715732 (Feb. 8, 2007); 12715736 (Feb. 8, 2007); 13320183 (Feb. 8, 2007); 19818639 (Dec. 5, 2007); 19851977 (Dec. 5, 2007); 22136223 (Dec. 5, 2007); 22664816 (no longer available online); 24777415-24777421 (May 12, 2008); 24777776-24777778 (May 12, 2008).
Rad-Moghadam et al., 2006, One-pot Three-component Synthesis of 2-Substituted 4-Aminoquinazolines, J. Heterocyclic Chem. 43:913-916.
Raleigh et al., 1999, Pharmacokinetics of Isotretinoin (ISO) in Rats Following Oral Dosing or Aerosol Inhalation, British J. Cancer 80, Suppl. 2:96 Abstract No. P269.
Rasmussen et al., 1978, The Electrophilic Addition of Chlorosulfonyl Isocyanate to Ketones. A Convenient Synthesis of Oxazines, Oxathiazines, and Uracils, J. Org. Chem. 38:2114-2115.
Reddy et al., 1988, An Efficient Synthesis of 3,4-Dihydro-4-Imino-2(1H)-Quinazolinones, Synth Commun. 18:525-530 (1988).
Robinson et al., 2006, Sulfonamide Ligands Attained through Opening of Saccharin Derivatives, Eur. J. Org. Chem. 19:4483-4489.
Rodriguez-Hahn et al., 1984, A Study of the Thorpe-Ziegler Reaction in Very Mild Conditions, Synth Commun. 14:967-972.
Rosowsky et al., 1966, Quinazolines. III. Synthesis of 1,3-Diaminobenzo[f]quinazoline and Related Compounds, J. Org. Chem. 31:2607-2613.
Roy et al., 2006, Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity, J. Org. Chem. 71:382-385.
Saudek et al. 1989, A Preliminary Trial of the Programmable Implantable Medication System for Insulin Delivery, N. Engl. J Med. 321:574-579.
Seijas et al., 2000, Microwave enhanced synthesis of 4-aminoquinazolines, Tetrahedron Lett. 41:2215-2217.
Sharma et al., 2006, Synthesis and QSAR studies on 5-[2-(2-methylprop 1-enyl)-1H benzimidazol-lyl]-4,6-diphenyl-pyrimidin-2-(5H)-thione derivatives as antibacterial agents, Eur. J. Med. Chem. 41:833-840.
Silve et al., Nov. 2005, Delineating a $Ca^{2+}$ Binding Pocket within the Venus Flytrap Module of the Human Calcium Sensing Receptor, The Journal of Biological Chemistry, 280:37917-37923.
Smith et al., 2001, March's Advanced Organic Chemistry, pp. 479-480, 506-507, 510-511, 576-577, 862-865, 1179-1180 and 1552-1553, $5^{th}$ Edition, John Wiley & Sons, Inc., 2001.
Spatola, 1983, Peptide Backbone Modifications: a structure-activity analysis of peptides containing amide bond surrogates, In Chemistry and Biochemistry of Amino Acids, Peptides and Proteins, 7:267-357, Marcell Dekker, NY.
Srivastava et al., 1999, Solid Phase Synthesis of Structurally Diverse Pyrimido[4,5-d] Pyrimidines for the Potential Use in Combinatorial Chemistry, Bioorg. Med. Chem. Lett. 9:965-966.
STN CAS Registry of 92932-14-4, referencing ES53119 (1985) and Goya et al. Archiv der Pharmazie (1984) 317(9).
Thurmond et al., 2008, Synthesis and biological Evaluation of Novel 2,4-diaminoquinazoline Derivatives as SMN2 Promoter Activator for the potential Treatment of spinal Muscular Atrophy, J. Med. Chem. 51(3):449-469.
Tripathi et al., 1987, Reaction of Flavanones with Chlorosulphonyl Isocyanate, Indian J. Chem. Sect. B 26B:1082-1083.

(56) References Cited

OTHER PUBLICATIONS

Trivedi et al., 1989, C2,N[6]—Distributed Adenosines: Synthesis and Structure-Activity Relationships, J. Med. Chem. 32(8):1667-1673.
Tunaley, 1989, Chapter 11. Perceptual Characteristics of Sweeteners, in Progress in Sweeteners, Greby ed., Elsevier Applied Science, London and New York. pp. 291-309.
Uehling et al., 2006, Biarylaniline Phenethanolamines as Potent and Selective $\beta_3$ Adrenergic Receptor Agonists, J. Med. Chem. 49(9):2758-2771.
Verma et al., 2000, Osmotically Controlled Oral Drug Delivery, Drug Dev. Ind. Pharm. 26:695-708.
Vippagunta et al., 2001, Crystalline solids, Adv. Drug Deliv. Rev. 48:3-26.
Wiet et al., 1993, Fat concentration affects sweetness and senory profiles of sucrose, sucralose, and aspartame, Journal of Food Science, 58(3):599-602.
Wiet et al., 1997, Does chemical modification of tastants merely enhance their intrinsic taste qualities? Food Chem. 58(4):305-311.
Wilson et al., 2007, Synthesis of 5-deazaflavin derivatives and their activation of p53 in cells, Bioorg. & Med. Chem. 15:77-86.
Wilson, 2000, Traceless Solid-Phase Synthesis of 2,4-Diaminoquinazolines, Org. Lett. 3:585-588.
Winkler et al., 2005, Synthesis and microbial transformation of β-amino nitriles, Tetrahedron, 61:4249-4260.
Wright, 1964, The Reaction of Sulfamide with α- and β-Diketones. The Preparation of 1,2,5-Thiadiazole 1,1-Dioxides and 1,2,6-Thiadiazine 1,1-Dioxides, J. Org. Chem. 29:1905-1909.
Wright, 1965, The Synthesis of 2,1,3-Benzothiadiazine 2,2-Dioxides and 1,2,3-Benzoxathiazine 2,2-Dioxides, J. Org. Chem. 30(11):3960-3962.
Xu et al., 1999, Purine and Pyrididine Nucleotides Inhibit a Noninactivating K+ Current and Depolarize Adrenal Cortical Cells through a G Protein-coupled Receptor, Mol. Pharmacol. 55:364-376.
Xu et al., 2006, Oxidative cyclization of N-alkyl-o-methyl-arenesulfonamides to biologically important saccharin derivatives, Tetrahedron 62:7902-7910.
Yamada et al., 2005, Discovery of Novel and Potent Small-Molecule inhibitors of NO and Cytokine Production as Antisepsis Agents: Synthesis and Biological Activity of Alkyl 6-(N-Substituted sulfamoyl)cyclohex-1-ene-1-carboxylate, J. Med. Chem. 48(23):7457-7467.
Yoshizawa et al., 2002, Efficient solvent-free Thrope reaction, Green Chem. 4:68-70.
Zunszain et al., 2005, Search for the pharmacophore in prazosin for Transport-P, Bioorg. & Med. Chem. 13:3681-3689.
Extended European Search Report, EP appl. No. 09803521.5, 16 pages (Apr. 2, 2013).
International Search Report based on International Patent Application No. PCT/US09/052048, mailed on Mar. 3, 2010.
Written Opinion of International Search Authority based on International Patent Application No. PCT/US09/052048, mailed on Mar. 3, 2010.
Zhu et al., 2006, The chemical development of CHIR-258, Chimia, 60:584-592.
Bassoli et al., 2000, Chapter 3: A rational design of new intensive sweeteners from natural compounds, in Lanzotti et al., eds., Flavour and Fragrance Chemistry, Kluwer Academic Publishers, the Netherlands, pp. 27-36.
Suami et al., 1998, Molecular mechanisms of sweet taste 8: saccharin, acesulfame-K, cyclamate and their derivatives, Food Chemistry, 63(3):391-396.

* cited by examiner

PROCESSES AND INTERMEDIATES FOR MAKING SWEET TASTE ENHANCERS

CROSS REFERENCE TO RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 14/053,897, filed Oct. 15, 2013, assigned U.S. Pat. No. 9,382,196, which is a divisional of U.S. patent application Ser. No. 13/056,843, filed Jun. 20, 2011, now as U.S. Pat. No. 8,586,733, which is a U.S. National Stage application of International Application No. PCT/US2009/052048, filed Jul. 29, 2009, which claims the benefit of U.S. Provisional Application No. 61/085,206, filed 5 Jul. 31, 2008 and entitled "PROCESSES AND INTERMEDIATES FOR MAKING SWEET TASTE ENHANCERS", and U.S. Provisional Application No. 61/167,654, filed Apr. 8, 2009 and entitled "PROCESSES AND INTERMEDIATES FOR MAKING SWEET TASTE ENHANCERS" each of which is incorporated herein by reference in its entirety.

FIELD OF THE INVENTION

The present invention relates to intermediates and processes/methods for preparing compounds having structural formula (I) or their salts, as described below.

BACKGROUND OF THE INVENTION

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989)).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. In contrast, some high-intensity sweeteners, notably sucralose (1,6-dichloro-1,6-dideoxy-β-D-fructofuranosyl-4-chloro-4-deoxy-α-D-galacto-pyranoside) and aspartame (N-L-α-aspartyl-L-phenylalanine methyl ester), display clean sweet tastes very similar to that of sugar (S. G. Wiet and G. A. Miller, Food Chemistry, 58(4):305-311 (1997)). In other words, these compounds are not characterized as having bitter or metallic aftertastes.

However, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

Hence, there is a need for sweet taste enhancers with desirable characteristics. It has been reported that an extracellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds including the compounds having structural Formula (I) have been reported to have superior sweet taste enhancing properties and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. patent application Ser. No. 11/836,074, entitled "Modulation of Chemosensory Receptors and Ligands Associated Therewith", filed Aug. 8, 2007; (3) U.S. Patent Application Ser. No. 61/027,410, entitled "Modulation of Chemosensory Receptors and Ligands Associated Therewith", filed Feb. 8, 2008; and (4) International Application No. PCT/US2008/065650, entitled "Modulation of Chemosensory Receptors and Ligands Associated Therewith", filed Jun. 3, 2008. The content of these applications are herein incorporated by reference in their entirety for all purposes.

Accordingly, the present invention provides intermediates and processes/methods improving the laboratory scale syntheses of these sweet taste enhancers and the preparation of their salts.

SUMMARY OF THE INVENTION

In one embodiment, the present invention provides a process of preparing a compound having structural Formula (I):

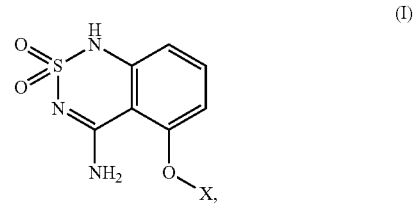

which comprises reacting a compound having structural Formula (II)

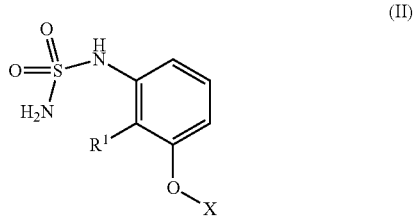

with a base or an activating reagent, wherein $R^1$ is —CN or —C(O)NH$_2$; and X is alkyl, substituted alkyl, alkenyl, substituted alkenyl, heteroalkyl, substituted heteroalkyl, heteroalkenyl, or substituted heteroalkenyl.

In one embodiment, the present invention provides a process of preparing a compound having structural Formula (I):

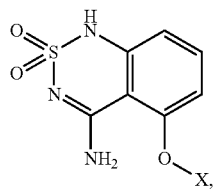

which comprises reacting a compound having structural Formula (III)

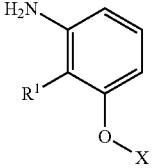

with $NH_2S(O)_2NH_2$ or $Cl-S(O)_2-NH_2$ optionally in the presence of a base, to provide directly the compound having structural Formula (I), or alternatively to provide the compound having structural formula (II) which is further reacted with an inorganic base or an activating reagent to provide the compound having structural Formula (I), wherein $R^1$ is —CN or —C(O)NH$_2$; and X is alkyl, substituted alkyl, alkenyl, substituted alkenyl, heteroalkyl, substituted heteroalkyl, heteroalkenyl, or substituted heteroalkenyl.

In one embodiment, the present invention provides a process of preparing a compound having structural Formula (I):

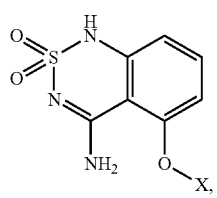

comprising reacting a compound having structural Formula (VII)

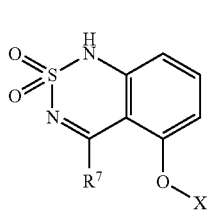

with $NH_3$ or $NH_3 \cdot H_2O$; wherein X is alkyl, substituted alkyl, alkenyl, substituted alkenyl, heteroalkyl, substituted heteroalkyl, heteroalkenyl, or substituted heteroalkenyl; and $R^7$ is a leaving group selected from the group consisting of halo, -OMs, OTs, and OTf.

In one embodiment, the present invention provides a process of preparing a compound having structural Formula (Ib):

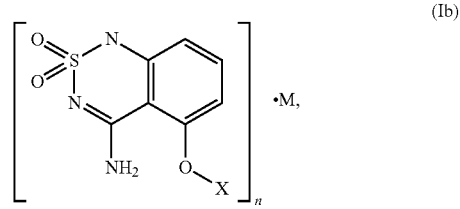

comprising reacting a compound having structural Formula (I)

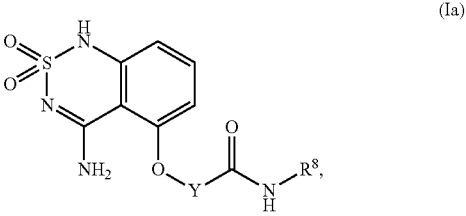

with an alkali metal- or alkaline earth metal-based inorganic base, wherein M is a cation of alkali metal or alkaline earth metal; X is alkyl, substituted alkyl, alkenyl, substituted alkenyl, heteroalkyl, substituted heteroalkyl, heteroalkenyl, or substituted heteroalkenyl; n is 1, when M is a cation of alkali metal; and n is 2, when M is a cation of alkaline earth metal.

In one embodiment, the present invention provides a process of preparing a compound having structural Formula (Ia):

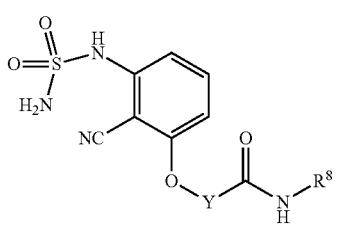

comprising reacting a compound having structural Formula (IIc1)

with a hydroxide or alkoxide base in an aqueous solution at a temperature ranging from about 25 to about 95° C., wherein Y is C1-C12 alkylene or C1-C12 alkenylene; and $R^8$ is C1-C12 alkyl.

In one embodiment, the present invention provides a process of preparing a compound having structural Formula (IIc1):

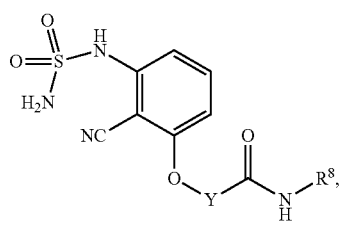

comprising adding a solution of a compound having structural Formula (IIIc1)

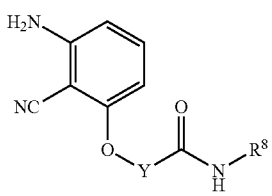

in a mixed solvent of methylene chloride and dimethylacetamide to a solution of Cl—S(O)$_2$—NH$_2$ in methylene chloride to form a reaction mixture, and maintaining the reaction mixture at about room temperature for about 6 to about 18 hours; wherein Y is C1-C12 alkylene or C1-C12 alkenylene; and $R^8$ is C1-C12 alkyl.

In one embodiment, the present invention provides a process of preparing a compound having structural Formula (IIIc1):

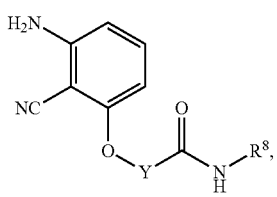

comprising reacting HO—Y—C(O)—NHR$^8$ with

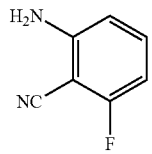

in the presence of a base to form a first mixture solution; concentrating the first mixture solution to form a concentrated first mixture solution, wherein the volume of the concentrated first mixture solution is equivalent to or less than about 50% of the volume of the first mixture solution; diluting the concentrated first mixture solution with an ether to form a second mixture solution; concentrating the second mixture solution to form a concentrated second mixture solution, wherein the volume of the concentrated second mixture solution is equivalent to or less than about 50% of the volume of the second mixture solution; diluting the concentrated second mixture solution with ethyl acetate to form a third mixture solution, and concentrating the third mixture solution to form a concentrated third mixture solution; wherein Y is C1-C12 alkylene or C1-C12 alkenylene; and $R^8$ is C1-C12 alkyl.

In one embodiment, the present invention provides a process of preparing sulfamoyl chloride:

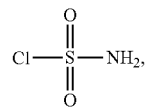

comprising reacting chlorosulfonyl isocyanate with formic acid in the presence of an organic amine.

In one embodiment, the present invention provides a process of preparing a compound having structural formula (XI):

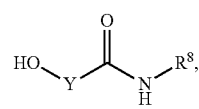

comprising reacting a compound having structural formula (XII):

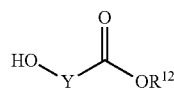

with NH$_2$R$^8$ under a pressure higher than the standard atmospheric pressure at a temperature higher than about 80° C., wherein Y is C1-C12 alkylene or C1-C12 alkenylene; and $R^8$ and $R^{12}$ are independently C1-C12 alkyl.

DETAILED DESCRIPTION OF THE INVENTION

The present invention provides intermediates and methods/processes for preparing compounds having structural Formula (I) and their salts at large scale, such as, for example, kilogram to metric ton scale. The advantages of the present intermediates and methods/processes include at least the following: (a) enabling synthesis of compounds of Formula (I) from building blocks that are commercially available in kg to metric ton quantities and at an affordable price; (b) enabling synthesis of compounds of Formula (I) using reagents and solvents that are compatible with large scale process; (c) improving overall synthesis yield to decrease overall cost as compared to the laboratory synthesis; (d) purifying intermediates using crystallization techniques instead of chromatography on silica gel and thereby substantially reducing the time and cost of production.

Prior to specifically describing embodiments and examples of the present invention, the following definitions are provided.

DEFINITIONS

"Activating reagent", as used herein, denotes a reagent which can react with one of the starting materials of a chemical reaction to form one or more active intermediate which subsequently facilitates the completion of the reaction. The active intermediate may not be stable enough to be separated and characterized. Examples of the activating reagent include, but are not limited to the coupling reagents used in amide/peptide synthesis, such as carbodiimide compound (EDC, DCC, DIC, and the like) and benzotriazole compounds (such as HOBt and HOAt); certain oxides and chloride (such as $P_2O_5$ and $POCl_3$); a reagent which react with a molecule to form a leaving group (such as MsCl, $Tf_2O$, and reagents for Mitsunobu reaction); and etc.

"Alkali metal", as used herein, denotes a series of elements comprising Group 1 (IUPAC style) of the periodic table including lithium (Li), sodium (Na), potassium (K), rubidium (Rb), cesium (Cs), and francium (Fr). Preferably, the alkali metal is Li, Na, or K.

"Alkaline earth metal", as used herein, denotes a series of elements comprising Group 2 (IUPAC style) of the periodic table including beryllium (Be), magnesium (Mg), calcium (Ca), strontium (Sr), barium (Ba) and radium (Ra). Preferably, the alkali metal is Mg or Ca.

"Ammonia" refers to the gas having formula $NH_3$ or a solution thereof. Preferably, ammonia is an aqueous solution of $NH_3$.

By "Alkyl", it is meant a univalent group derived from a saturated hydrocarbon by removing one hydrogen atom. The saturated hydrocarbon may contain normal, secondary, or tertiary carbon atoms. These carbon atoms may be arranged in straight or branched chain, or in cyclic ring, or a combination thereof. For example, an alkyl group can have 1 to 20 carbon atoms (i.e, C1-C20 alkyl), 1 to 12 carbon atoms (i.e., C1-C12 alkyl), or 1 to 6 carbon atoms (i.e., C1-C6 alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkylene" refers to a divalent group derived from an alkyl by removing one hydrogen atom. That is, "alkylene" can be a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 12 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" refers to a univalent group derived from a hydrocarbon by removing one hydrogen atom wherein the hydrocarbon contains at least one carbon-to-carbon double bond. For example, an alkenyl group can have 1 to 20 carbon atoms (i.e, $C_1$-$C_{20}$ alkenyl), 1 to 12 carbon atoms (i.e., C1-C12 alkenyl), or 1 to 6 carbon atoms (i.e., C1-C6 alkenyl). Typical alkenyl groups include, but are not limited to, ethenyl, prop-1-en-1-yl, prop-1-en-2-yl, prop-2-en-1-yl (allyl), cycloprop-1-en-1-yl; cycloprop-2-en-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, and the like.

"Alkenylene" refers to a divalent group derived from an alkenyl by removing one hydrogen atom. That is, "alkenylene" can be an unsaturated, branched or straight chain or cyclic unsaturated hydrocarbon radical having two monovalent radical centers derived by the removal of two hydrogen atoms from the same or two different carbon atoms of a parent alkene.

"Alkoxyl" refers to a monovalent radical —OR wherein R is an alkyl or alkenyl.

"Base" refers to a substance whose molecule or ion can combine with a proton (hydrogen ion), a substance capable of donating a pair of electrons (to an acid) for the formation of a coordinate covalent bond. A base can be inorganic or organic. Examples of base include, but are not limited to sodium hydroxide, sodium hydride, ammonia, 1,8-diazabicyclo[5.4.0]undec-7-ene (DBU), and 4-dimethylaminopyridine (DMAP).

"Halo" refers to a univalent group derived from a halogen element including fluorine, chlorine, bromine, iodine, and astatine.

By "leaving group", it is meant a functional group capable of detaching from a chemical substance. Examples of leaving group include, but are not limited to alkoxy, hydroxyl, carboxylate, fluoro, chloro, bromo, iodo, azide, thiocyanate, nitro, mesylate (-OMs), tosylate (OTs), triflate (OTf), and etc.

"Heteroalkyl" or "heteroalkenyl" refers to alkyl or alkenyl, respectively, in which one or more of the carbon atoms (and optionally any associated hydrogen atoms), are each, independently of one another, replaced with the same or different heteroatoms or heteroatomic groups. Similarly, "heteroalkylene," or "heteroalkenylene" refers to alkylene or alkenylene, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —$S(O)_2$—, —S(O)NH—, —$S(O)_2$NH— and the like and combinations thereof. The heteroatoms or heteroatomic groups may be placed at any interior position of the alkyl or alkenyl. Typical heteroatomic groups which can be included in these groups include, but are not limited to, —O—, —S—, —O—O—, —S—S—, —O—S—, —$N(R^a)_2$—, =N—N=, —N=N—$N(R^a)_2$, —$PR^a$—$P(O)_2$—, —POR$^a$—, —O—P(O)$_2$—, —SO—, —SO$_2$—, —Sn(R$^a$)$_2$— and the like, where each R$^a$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or a protecting group.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

The term "substituted", when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —R$^c$, halo, —O$^-$, =O, —OR$^b$, —SR$^b$, —S$^-$, =S, —N(R$^d$)$_2$, =NR$^b$, =N—OR$^b$, trihalomethyl, —CF$_3$, —CN, —OCN, —SCN, —NO, —NO$_2$, =N$_2$, —N$_3$, —S(O)$_2$R$^b$, —S(O)$_2$NR$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O)$_2$, —P(O)(OR$^b$)(O), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)N(R$^d$)$_2$, —C(NR$^b$)N(R$^d$)$_2$), OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)N(R$^d$)$_2$, —NR$^b$C(NR$^b$)R$^b$ and —NR$^b$C(NR$^b$)N(R$^d$)$_2$, where R$^c$ is selected from the group consisting of alkyl, cycloalkyl, heteroalkyl, cycloheteroalkyl, aryl, arylalkyl, heteroaryl and heteroarylalkyl; each R$^b$ is independently hydrogen, a protecting group, or R$^c$; and each R$^d$ is independently R$^b$ or alternatively, the two R$^d$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —N(R$^d$)$_2$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$, -alkylene-C(O)N(R$^d$)$_2$, and —CH$_2$—CH$_2$—C(O)—CH$_3$. The one or more substituent groups, taken together with the atoms to which they are bonded, may form a cyclic ring including cycloalkyl and cycloheteroalkyl.

The term "alcohol" herein means an organic compound in which a hydroxyl group (—OH) is bound to a carbon atom of an alkyl or substituted alkyl group. The alcohol includes primary, secondary, and tertiary alcohols. Examples of alcohol include, but are not limited to, methanol, ethanol, n-propanol, isopropanol, n-butanol, s-butanol, and t-butanol. The alcohol may be further optionally substituted.

The term "alkane hydrocarbon" herein means an organic compound or a mixture of organic compounds which consist of hydrogen and carbon and contain no or trace amount of unsaturated carbon-carbon bond. Examples of alkane hydrocarbon include, but are not limited to, hexanes and heptanes.

The term "base" refers to a substance that can accept protons. Examples of the base include, but are not limited to sodium hydride (NaH), potassium hydride (KH), sodium hexamethyldisilazane (NaHMDS), potassium hexamethyldisilazane (KHMDS), sodium tert-butoxide (NaO$^t$Bu), potassium tert-butoxide (KO$^t$Bu), sodium hydroxide, potassium hydroxide, calcium hydroxide, sodium methoxide, sodium ethoxide, sodium tert-butoxide, and a mixture thereof. The term "hydroxide or alkoxide base" refers to a base, the disassociation of which produces the anion OH$^-$ or RO$^-$, where R is an alkyl group. Examples of the hydroxide base include, but are not limited to, sodium hydroxide, potassium hydroxide, calcium hydroxide, and a mixture thereof. Examples of the alkoxide base include, but are not limited to, sodium methoxide, sodium ethoxide, sodium tert-butoxide, and a mixture thereof.

By "room temperature", it is meant the normal temperature of room in which people live or conduct business. In one example, the room temperature denotes a temperature ranging from about 20 to about 25° C.

As used herein, "polar aprotic solvent" refers to a solvent that shares ion dissolving power with a protic solvent but lack an acidic hydrogen. A protic solvent is a solvent that has a hydrogen atom bound to an oxygen as in a hydroxyl group or a nitrogen as in an amine group. More generally, any molecular solvent which contains dissociable H$^+$, such as hydrogen fluoride, is called a protic solvent. The molecules of such protic solvents can donate an H$^+$ (proton). Conversely, aprotic solvents cannot donate hydrogen. The aprotic solvents generally have high dielectric constants and high polarity. Examples are dimethyl sulfoxide (DMSO), dimethylformamide (DMF), dioxane, hexamethylphosphorotriamide (HMPTA), and tetrahydrofuran (THF).

The term "organic amine" herein denotes a compound having structural formula N(R)$_3$, wherein each R is independently hydrogen, alkyl, alkenyl, aryl, heteroaryl, heteroalkyl, arylalkyl, or heteroarylalkyl, or alternatively, two of R, together with the nitrogen atom to which they are attached, form a heterocyclic ring. Examples of organic amine include, but are not limited to, methylamine, dimethylamine, diethylamine, methylethylamine, triethylamine, diisoproylethylamine (DIEA), morpholine, peperidine, and combinations thereof.

The term "portionwise", as used herein, describes a controlled discharge of a substance for adding to another substance or filling a reactor or container. The controlled discharge may be discrete or continuous. The portionwise discharge of a substance may include discharge the substance in one portion or in multiple portions. In one example, a liquid is added to a reaction mixture over an extended period of time by controlling the discharging speed of the liquid. In another example, a solid material is added to a reaction mixture by dividing the solid material in multiple portions and discharge the solid material one portion at a time.

Processes/Methods

The present invention provides methods/processes for preparing the compounds having structural Formula (I) amenable to large scale process.

In one embodiment, the present invention provides a process of preparing a compound having structural Formula (I):

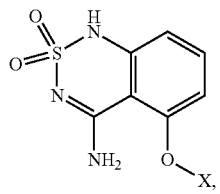
(I)

which comprises reacting a compound having structural Formula (II)

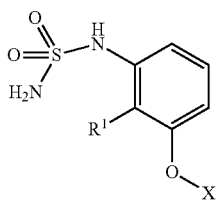
(II)

with a base or an activating reagent, wherein R¹ is —CN or —C(O)NH₂; and X is alkyl, substituted alkyl, alkenyl, substituted alkenyl, heteroalkyl, substituted heteroalkyl, heteroalkenyl, or substituted heteroalkenyl. For example, this process may comprise reacting a compound having structural Formula (IIa)

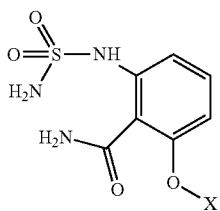
(IIa)

with an activating reagent to provide the compound of Formula (I). Alternatively, this process may comprise reacting a compound having structural Formula (IIb)

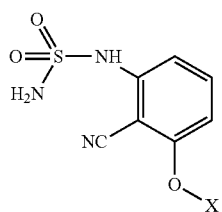
(IIb)

with a base to provide the compound of Formula (I).

In one embodiment, the present invention provides a process of preparing a compound having structural Formula (I):

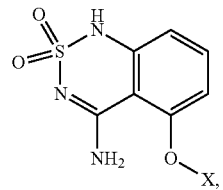
(I)

which comprises reacting a compound having structural Formula (III)

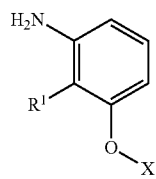
(III)

with NH₂S(O)₂NH₂ or Cl—S(O)₂—NH₂ optionally in the presence of a base, to provide directly the compound having structural Formula (I), or alternatively to provide the compound having structural formula (II) of claim 1 which is further reacted with an inorganic base or an activating reagent to provide the compound having structural Formula (I), wherein R¹ is —CN or —C(O)NH₂; and X is alkyl, substituted alkyl, alkenyl, substituted alkenyl, heteroalkyl, substituted heteroalkyl, heteroalkenyl, or substituted heteroalkenyl. For example, this process may comprise reacting a compound having structural Formula (IIIa):

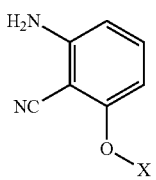
(IIIa)

with NH₂—S(O)₂—NH₂ in the presence of a base to provide the compound of Formula (I). Alternatively, this process may comprise reacting a compound having structural Formula (IIIa)

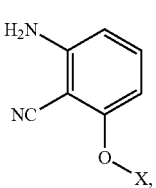
(IIIa)

with Cl—S(O)₂—NH₂ to provide a compound having structural Formula (In)

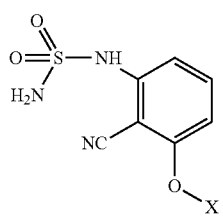

(IIb)

which is further reacted with a base to provide the compound having structural Formula (I). Alternatively, this process may comprise reacting a compound having structural Formula (IIIb)

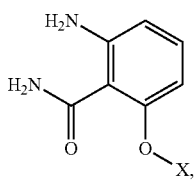

(IIIb)

with Cl—S(O)$_2$—NH$_2$ to provide a compound having structural Formula (IIa), (IIa)

which is further reacted with an activating reagent to provide the compound having structural Formula (I).

In one embodiment, the present invention provides a process of preparing a compound having structural Formula (IIIb):

(IIIb)

which comprises hydrolyzing a compound having structural formula (IIIa)

(IIIa)

wherein X is alkyl, substituted alkyl, alkenyl, substituted alkenyl, heteroalkyl, substituted heteroalkyl, heteroalkenyl, or substituted heteroalkenyl.

In one embodiment, the present invention provides a process of preparing a compound having structural Formula (IIIb):

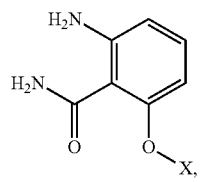

(IIIb)

which comprises treating a compound having structural formula (IIIc) with ammonia, (IIIc)

wherein X is alkyl, substituted alkyl, alkenyl, substituted alkenyl, heteroalkyl, substituted heteroalkyl, heteroalkenyl, or substituted heteroalkenyl; and R$^3$ is halo or alkoxyl.

In one embodiment, the present invention provides a process of preparing a compound having structural Formula (IIIa):

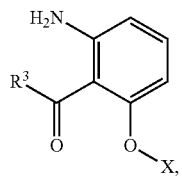

(IIIa)

which comprises reducing a compound having structural Formula (IV), or treating a compound having structural Formula (IV) with ammonia,

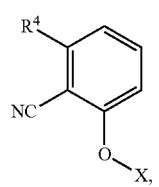

(IV)

wherein R$^4$ is nitro or halo; and X is alkyl, substituted alkyl, alkenyl, substituted alkenyl, heteroalkyl, substituted heteroalkyl, heteroalkenyl, or substituted heteroalkenyl. For example, this process may comprise reducing the compound having structural Formula (IV) to provide the compound of Formula (IIIa), wherein R$^4$ is nitro. Alternatively, the process may comprise treating the compound having structural Formula (IV) with ammonia to provide the compound of Formula (IIIa), wherein R$^4$ is halo.

In one embodiment, the present invention provides a process of preparing a compound having structural Formula (IV):

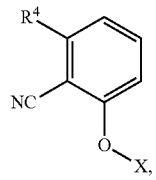
(IV)

comprising reacting a compound having structural Formula (V)

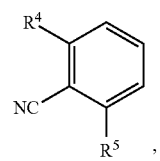
(V)

with X—OH in the presence of a base; wherein $R^4$ is nitro, —$NH_2$, or halo; X is alkyl, substituted alkyl, alkenyl, substituted alkenyl, heteroalkyl, substituted heteroalkyl, heteroalkenyl, or substituted heteroalkenyl; and $R^5$ is nitro or halo.

In one embodiment, the present invention provides a process of preparing a compound having structural Formula (IV):

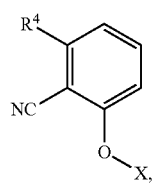
(IV)

comprising reacting a compound having structural Formula (VI)

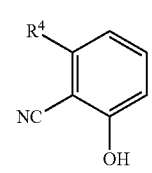
(VI)

with X—$R^6$ in the presence of a base or an activating reagent; wherein $R^4$ is nitro, —$NH_2$, or halo; X is alkyl, substituted alkyl, alkenyl, substituted alkenyl, heteroalkyl, substituted heteroalkyl, heteroalkenyl, or substituted heteroalkenyl; and $R^6$ is a leaving group selected from halo, -OMs, OTs, and -OTf.

In one embodiment, the present invention provides a process of preparing a compound having structural Formula (I):

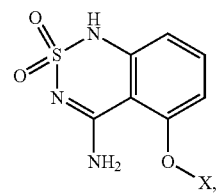
(I)

comprising reacting a compound having structural Formula (VII)

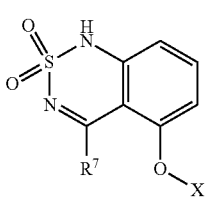
(VII)

with $NH_3$ or $NH_3 \cdot H_2O$; wherein X is alkyl, substituted alkyl, alkenyl, substituted alkenyl, heteroalkyl, substituted heteroalkyl, heteroalkenyl, or substituted heteroalkenyl; and $R^7$ is a leaving group selected from the group consisting of halo, -OMs, -OTs, and -OTf.

In preferred embodiments of the above described processes, X is C1-C12 alkyl, C1-C12 heteroalkyl, C1-C12 alkenyl, C1-C12 heteroalkenyl, —Y—C(O)—$OR^2$, or —Y—C(O)—NH—$R^2$; Y is C1-C12 alkylene or C1-C12 alkenylene; and each $R^2$ is independently hydrogen or C1-C12 alkyl.

In one embodiment, the present invention provides a process of preparing a compound having structural Formula (Ia):

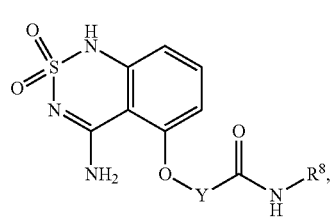
(Ia)

comprising reacting a compound having structural Formula (VIII)

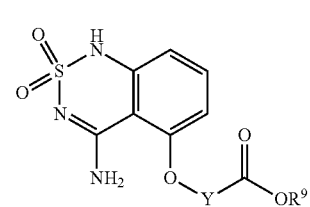
(VIII)

with $R^8$—$NH_2$, in the presence of an activating reagent; wherein Y is C1-C12 alkylene or C1-C12 alkenylene; $R^8$ is C1-C12 alkyl; and $R^9$ is hydrogen or C1-C12 alkyl.

In one embodiment, the present invention provides a process of preparing a compound having structural Formula (IIc):

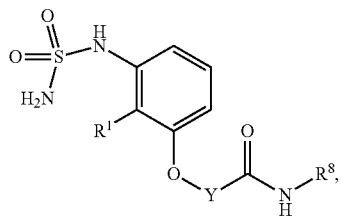

comprising reacting a compound having structural Formula (IX)

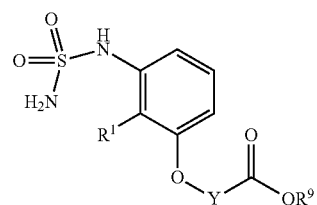

with R⁸—NH₂, in the presence of an activating reagent; wherein R¹ is —CN or —C(O)NH₂; each R² is independently hydrogen or C1-C12 alkyl; Y is C1-C12 alkylene or C1-C12 alkenylene; R⁸ is C1-C12 alkyl; and R⁹ is hydrogen or C1-C12 alkyl.

In one embodiment, the present invention provides a process of preparing a compound having structural Formula (IIIc):

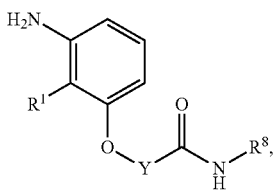

comprising reacting a compound having structural Formula (X)

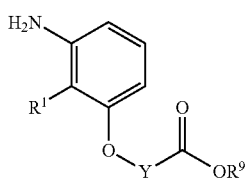

with R⁸—NH₂, in the presence of an activating reagent; wherein R¹ is —CN or —C(O)NH₂; Y is C1-C12 alkylene or C1-C12 alkenylene; and R⁸ is C1-C12 alkyl; and R⁹ is hydrogen or C1-C12 alkyl.

In one embodiment, the present invention provides a process of preparing a compound having a structural formula of R⁶—Y—C(O)—NH—R² comprising reacting a compound having a structural formula of R⁶—Y—C(O)—R¹⁰ with R²—NH₂, optionally in the presence of an activating reagent or a base; wherein R² is hydrogen or C1-C12 alkyl; R⁶ is halo or hydroxyl; Y is C1-C12 alkylene or C1-C12 alkenylene; R¹⁰ is a leaving group selected from the group consisting of halo, —OR¹¹, —O—C(=CH₂)—OR¹², and

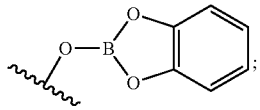 [SMILES: *OB1Oc2ccccc2O1]

R¹¹ is hydrogen or C1-C12 alkyl; and R¹² is C1-C12 alkyl.

In preferred embodiments of the above described processes, the compound having structural Formula (I) is

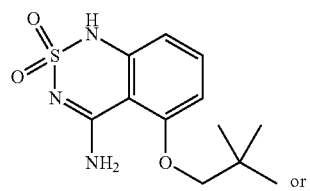

or

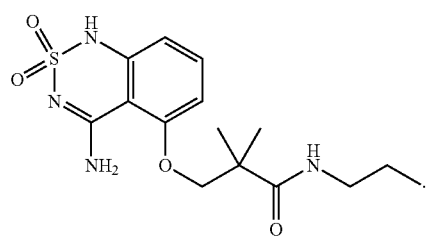

In one embodiment, the present invention provides syntheses of the sodium salt of the compounds having structural Formula (I) amenable to large scale process. It was observed that the sodium salts of the present compounds have improved physical properties especially with regard to improved solubility characteristics in specific solvents that are used to prepare stock solutions.

In one embodiment, the present invention provides a process of preparing a compound having structural Formula (Ib):

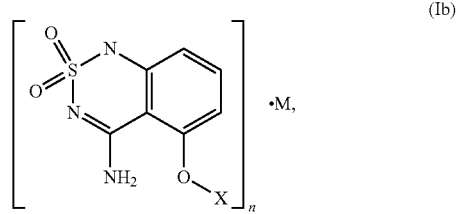

comprising reacting a compound having structural Formula (I)

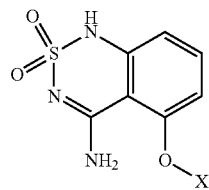
(I)

with an alkali metal- or alkaline earth metal-based inorganic base, wherein M is a cation of alkali metal or alkaline earth metal; X is alkyl, substituted alkyl, alkenyl, substituted alkenyl, heteroalkyl, substituted heteroalkyl, heteroalkenyl, or substituted heteroalkenyl; n is 1, when M is a cation of alkali metal; and n is 2, when M is a cation of alkaline earth metal. It is preferable that M is a cation of sodium. It is also preferable that X is C1-C12 alkyl, C1-C12 heteroalkyl, C1-C12 alkenyl, C1-C12 heteroalkenyl, —Y—C(O)—OR$^2$, or —Y—C(O)—NH—R$^2$; Y is C1-C12 alkylene or C1-C12 alkenylene; and each R$^2$ is independently hydrogen or C1-C12 alkyl.

In one embodiment of the above described processes, X is selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$.

In preferred embodiments of the above described processes, the compound having structural Formula (Ib) is

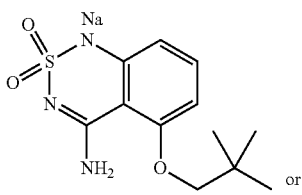
or

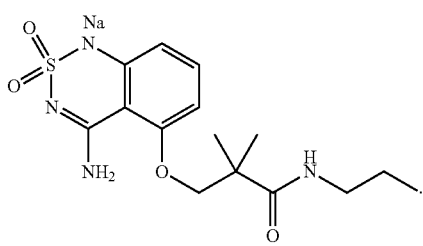

In one embodiment, the present invention provides a process of preparing a compound having structural Formula (Ia):

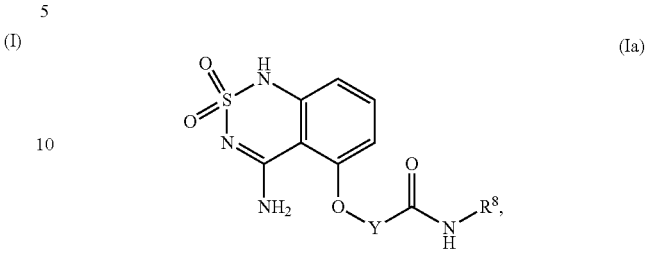
(Ia)

comprising reacting a compound having structural Formula (IIc1)

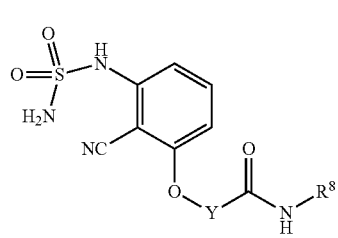
(IIc1)

with a hydroxide or alkoxide base in an aqueous solution at a temperature ranging from about 25 to about 95° C., wherein Y is C1-C12 alkylene or C1-C12 alkenylene; and R$^8$ is C1-C12 alkyl. In one specific embodiment, the hydroxide base is sodium hydroxide, potassium hydroxide, or a mixture thereof. In one embodiment, the reaction is carried out at a temperature ranging from about 35 to about 85° C. In one embodiment, the reaction is carried out at a temperature ranging from about 40 to about 70° C. Depending on the reaction conditions, such as temperature, scale, and concentration of the reaction mixture, the reaction may be carried out in about 4 to about 24 hours. In one embodiment, the reaction is carried out in about 8 to about 12 hours. In another embodiment, the reaction further comprises adding an alcohol to the reaction mixture of the compound having structural Formula (IIc1) and the hydroxide base to form an aqueous-alcohol mixture; and adding a hydrochloride solution to the aqueous-alcohol mixture to adjust the pH thereof to a range from about 4 to about 5. In one specific embodiment, the alcohol is methanol, ethanol, propanol, or a mixture thereof. In one embodiment, the hydrochloride solution is an aqueous solution. In one embodiment, the pH of the aqueous-alcohol mixture is adjusted to about 4.1, 4.2, 4.3, 4.4, 4.5, 4.6, 4.7, 4.8 or 4.9. In another embodiment, the reaction mixture of the compound having structural Formula (IIc1) and the hydroxide base is washed with an ether prior to the addition of the alcohol. Examples of the ether include, but are not limited to, dimethylether, diethylether, diisopropylether, di-tert-butyl ether, methyl tert-butyl ether, or a mixture thereof. In one specific embodiment, the compound having structural formula (Ia) is

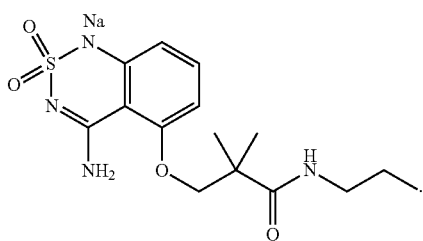

In one embodiment, the present invention provides a process of preparing a compound having structural Formula (IIc1):

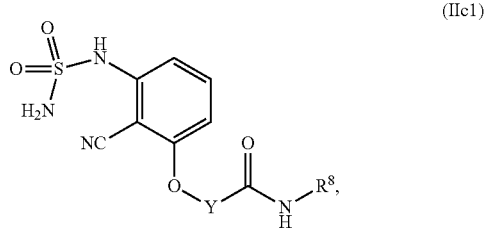

(IIc1)

comprising adding a solution of a compound having structural Formula (IIIc1)

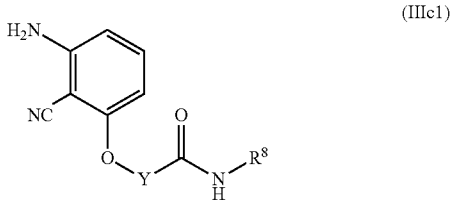

(IIIc1)

in a mixed solvent of methylene chloride and dimethylacetamide to a solution of Cl—S(O)₂—NH₂ (sulfamoyl chloride) in methylene chloride to form a reaction mixture; maintaining the reaction mixture at about room temperature for about 6 to about 18 hours; and extracting the reaction mixture with an aqueous solution of a hydroxide or alkoxide base to form an extracted basic solution wherein the compound having structural formula (IIc1) is stabilized; wherein Y is C1-C12 alkylene or C1-C12 alkenylene; and R⁸ is C1-C12 alkyl. In one embodiment, the hydroxide or alkoxide base is sodium hydroxide or potassium hydroxide. The volume ratio of methylene chloride and dimethylacetamide in the mixed solvent can be from about 1:100 to about 100:1. In one embodiment, methylene chloride and dimethylacetamide in the mixed solvent is in a ratio ranging from about 3:1 to about 30:1. In another embodiment, methylene chloride and dimethylacetamide in the mixed solvent is in a ratio ranging from about 4:1 to about 25:1. In another embodiment, methylene chloride and dimethylacetamide in the mixed solvent is in a ratio ranging from about 5:1 to about 20:1. In another embodiment, methylene chloride and dimethylacetamide in the mixed solvent is in a ratio ranging of about 16:1. In one embodiment, during addition of the solution of a compound having structural Formula (IIIc1) to the solution of Cl—S(O)₂—NH₂, the reaction mixture is maintained at a temperature ranging from about −5 to about 15° C. with the range from about 0 to about 10° C. more preferred. In one embodiment of the reaction, the solvent for the solution of Cl—S(O)₂—NH₂ is methylene chloride. In another embodiment, the solution of Cl—S(O)₂—NH₂ is in a mixed solvent of methylene chloride and acetonitrile. In one embodiment, the volume ratio of methylene chloride and acetonitrile ranges from about 5:1 to about 1:1. In another embodiment, the volume ratio of methylene chloride and acetonitrile ranges from about 4:1 to about 2:1. In one embodiment, after the reaction mixture of the compound having structural Formula (IIIc1) and Cl—S(O)₂—NH₂ is maintained at the room temperature for about 6 to about 18 hours and/or prior to the extraction of the reaction mixture with an aqueous solution of a hydroxide or alkoxide base, the reaction mixture is quenched with an aqueous solution of NaHCO₃. That is, an aqueous solution of NaHCO₃ is mixed with the reaction mixture to form a quenched mixture. The quenched mixture is maintained at a temperature of about 45° C. or below during the mixing process. In one embodiment, the temperature is maintained in a range from about 5 to about 35° C. with the range from about 10 to about 30° C. more preferred. In one embodiment, the aqueous solution of NaHCO₃ is a saturated aqueous solution of NaHCO₃. The mixing process may be carried out by adding the aqueous solution of NaHCO₃ to the reaction mixture or adding the reaction mixture to the aqueous solution of NaHCO₃.

In one embodiment, the present invention provides a process of preparing a compound having structural Formula (IIIc1):

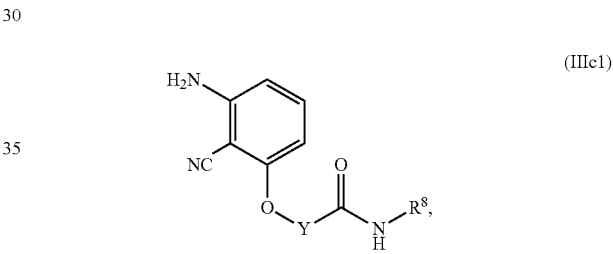

(IIIc1)

comprising reacting HO—Y—C(O)—NHR⁸ with 2-amino-6-fluorobenzonitrile in a polar aprotic solvent in the presence of a base to form a first mixture solution; concentrating the first mixture solution to form a concentrated first mixture solution, wherein the volume of the concentrated first mixture solution is equivalent to or less than about 50% of the volume of the first mixture solution; diluting the concentrated first mixture solution with an ether to form a second mixture solution; concentrating the second mixture solution to form a concentrated second mixture solution, wherein the volume of the concentrated second mixture solution is equivalent to or less than about 50% of the volume of the second mixture solution; diluting the concentrated second mixture solution with ethyl acetate to form a third mixture solution; and concentrating the third mixture solution to form a concentrated third mixture solution; wherein Y is C1-C12 alkylene or C1-C12 alkenylene; and R⁸ is C1-C12 alkyl. In one embodiment, the polar aprotic solvent is THF. Examples of the base include, but are not limited to sodium hydride (NaH), potassium hydride (KH), sodium hexamethyldisilazane (NaHMDS), potassium hexamethyldisilazane (KHMDS), sodium tert-butoxide (NaOᵗBu), potassium tert-butoxide (KOᵗBu), and a mixture thereof. Examples of the ether include, but are not limited to, dimethylether, diethylether, diisopropylether, di-tert-butyl ether, methyl tert-butyl ether, or a mixture thereof. In one embodiment, the reaction of HO—Y—C(O)—NHR⁸ with 2-amino-6-fluorobenzonitrile is carried out by mixing HO—Y—C(O)—NHR$^8$ with the base to form a reactive mixture, and then mixing the reactive mixture with 2-amino-6-fluorobenzonitrile. In one embodiment, the molar ratio of HO—Y—C(O)—NHR$^8$ to the base ranges from about 1:1 to about 2:1. In another embodiment, the molar ratio of HO—Y—C(O)—NHR$^8$ to the base ranges from about 1.2:1 to about 1.8:1. In another embodiment, the molar ratio of HO—Y—C(O)—NHR$^8$ to the base is about 1.5:1. In one embodiment, the above concentration steps are carried out by evaporating the solvent. The evaporation can be accomplished by any means known to one skilled in the art including, but are not limited to applying vacuum to the reaction mixture, elevating temperature of the reaction mixture, spinning the reaction mixture on a solid surface, stirring the reaction mixture, blowing air or other gas to the surface of the reaction mixture, and any combination thereof. Preferably, the temperature of the mixture solution during the evaporation process is not higher than about 50° C. In one embodiment, the evaporation is accomplished by rotovaping the reaction mixture at a temperature of about 50° C. or below with the temperature of about 40° C. or below more preferred. In one embodiment, the volume of any of the concentrated first, second, and third mixture solutions is equivalent to or less than about 45% of the volume of the first, second, and third mixture solutions, respectively. In one embodiment, the volume of any of the concentrated first, second, and third mixture solutions is equivalent to or less than about 35% of the volume of the first, second, and third mixture solutions, respectively. In one embodiment, the volume of any of the concentrated first, second, and third mixture solutions is equivalent to or less than about 30% of the volume of the first, second, and third mixture solutions, respectively. In one embodiment, the compound having structural Formula (IIIc1) precipitates out from the concentrated third mixture solution as solids. In one embodiment, the concentrated third mixture solution is diluted with an alkane hydrocarbon, and the solids of the compound having structural Formula (IIIc1) are filtered and washed with the alkane hydrocarbon. Examples of the alkane hydrocarbon include, but are not limited to, hexanes, heptanes, and mixtures thereof. In another embodiment, the second mixture solution is washed with water or an aqueous solution prior to the concentration of the second mixture solution.

In one embodiment, the present invention provides a process of preparing sulfamoyl chloride comprising reacting chlorosulfonyl isocyanate with formic acid in the presence of an organic amine. Examples of the organic amine include, but are not limited to, methylamine, dimethylamine, diethylamine, methylethylamine, triethylamine, diisoproylethylamine (DIEA), morpholine, peperidine, and combinations thereof. The chemical structures of sulfamoyl chloride, chlorosulfonyl isocyanate, and formic acid are shown below:

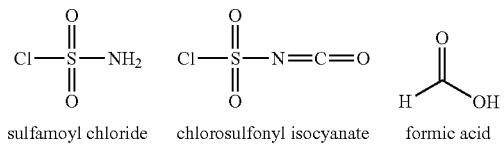 [SMILES: NS(=O)(=O)Cl ; O=C=NS(=O)(=O)Cl ; O=CO]

sulfamoyl chloride    chlorosulfonyl isocyanate    formic acid

In one embodiment, the reaction comprises portionwise adding a first mixture of formic acid and the organic amine to a second mixture of chlorosulfonyl isocyanate and the organic amine to form a reaction mixture. In one embodiment, the molar ratio of formic acid to the organic amine is from about 200:1 to about 10:1, and the molar ratio of chlorosulfonyl isocyanate to the organic amine is from about 200:1 to about 10:1. In another embodiment, the molar ratios of formic acid to the organic amine and chlorosulfonyl isocyanate to the organic amine are independently from about 150:1 to about 15:1. In another embodiment, the molar ratios of formic acid to the organic amine and chlorosulfonyl isocyanate to the organic amine are independently from about 100:1 to about 20:1. In one embodiment, the above first and second mixtures are independent in an organic solvent. In one specific embodiment, the above first and second mixtures are both in methylene chloride. In one embodiment, the reaction mixture is maintained at a temperature not higher than about 50° C. In another embodiment, the reaction mixture is maintained at a temperature ranging from about 0° C. to about 50° C. In another embodiment, the reaction mixture is maintained at a temperature ranging from about 10° C. to about 50° C. In another embodiment, the reaction mixture is maintained at a temperature ranging from about room temperature to about 50° C. In another embodiment, the reaction mixture is maintained at a temperature ranging from about 30° C. to about 45° C.

The reaction of converting chlorosulfonyl isocyanate to sulfamoyl chloride forms CO and $CO_2$ gas. Thus, depending on the scale of the reaction, the reaction process may be monitored and controlled. The reaction process can be monitored and controlled by any monitoring or controlling methods known to one skilled in the art including both instrumental and visual methods. In one embodiment, the first mixture is added to the second mixture in multiple portions, wherein the multiple portions comprise an initial portion and one or more subsequent portions, and each subsequent portion of the first mixture is not added to the second mixture until the reaction mixture ceases forming $CO_2$ gas. In one embodiment, the formation of $CO_2$ gas is monitored by a gas chromatograph (GC) method. In another embodiment, the formation of $CO_2$ gas is monitored by detecting the temperature change of the reaction. In another embodiment, the formation of $CO_2$ gas is monitored by visual observation. In another embodiment, the formation of $CO_2$ gas is monitored by a combination of GC, temperature detection, and visual observation.

In one embodiment, the present invention provides a process of preparing a compound having structural formula (XI):

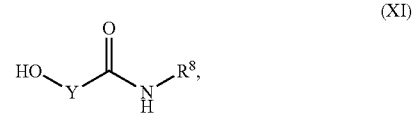

comprising reacting a compound having structural formula (XII):

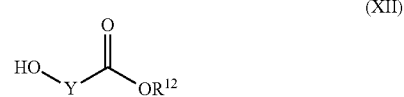

with $NH_2R^8$ under a pressure higher than the standard atmospheric pressure at a temperature higher than about 80°

C., wherein Y is C1-C12 alkylene or C1-C12 alkenylene; and $R^8$ and $R^{12}$ are independently C1-C12 alkyl. The pressurized condition can be created by any methods known to one skilled in the art. In one embodiment, the pressurized condition is created by running the reaction in a sealed reactor with heat. In another embodiment, the pressurized condition is created by pressurizing the reactor to a desired pressure with nitrogen. In one embodiment, the reaction was conducted at a temperature ranging from about 90° C. to about 200° C. In another embodiment, the reaction was conducted at a temperature ranging from about 100° C. to about 150° C. In another embodiment, the reaction was conducted at a temperature of about 120° C. In one embodiment, the reaction was conducted under a pressure of about 600 psig or below. In another embodiment, the reaction was conducted under a pressure of about 500 psig or below. In another embodiment, the reaction was conducted under a pressure of about 400 psig or below. In another embodiment, the reaction was conducted in a sealed reactor at a temperature of about 120° C. In one embodiment, the molar ratio of $NH_2R^8$ to a compound having structural formula (XI) is from about 1:1 to about 2:1. In another embodiment, the molar ratio of $NH_2R^8$ to a compound having structural formula (XI) is from about 1.2:1 to about 1.8:1. In another embodiment, the molar ratio of $NH_2R^8$ to a compound having structural formula (XI) is about 1.5:1.

In one embodiments of the above described processes, Y is selected from the group consisting of —CH$_2$—, —CH$_2$CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH$_2$CH$_2$CH$_2$CH$_2$CH$_2$—, —CH$_2$C(CH$_3$)$_2$CH$_2$—, —C(CH$_3$)$_2$CH$_2$CH$_2$—, —CH$_2$CH$_2$C(CH$_3$)$_2$—, —CH$_2$CH$_2$CH$_2$CH$_2$CH$_2$CH$_2$—, —CH$_2$C(CH$_3$)$_2$CH$_2$CH$_2$—, —CH$_2$CH$_2$C(CH$_3$)$_2$CH$_2$—, —CH$_2$CH$_2$CH$_2$C(CH$_3$)$_2$—, and —CH$_2$CH(CH$_2$CH$_3$)CH$_2$CH$_2$—.

In one embodiment of the above described processes, $R^8$ is methyl, ethyl, propyl, butyl, pentyl, or hexyl.

Intermediates

The present invention also provides synthetic intermediates for preparing the compounds having structural Formula (I) amenable to large scale process.

In one embodiment, the present invention provides a compound having structural Formula (II)

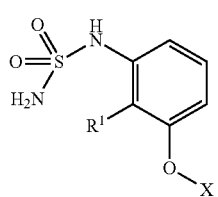

wherein $R^1$ is —CN, —C(O)OR$^2$, or —C(O)NH$_2$; X is alkyl, substituted alkyl, alkenyl, substituted alkenyl, heteroalkyl, substituted heteroalkyl, heteroalkenyl, or substituted heteroalkenyl; and $R^2$ is hydrogen or C1-C12 alkyl.

In one embodiment, the present invention provides a compound having structural Formula (III):

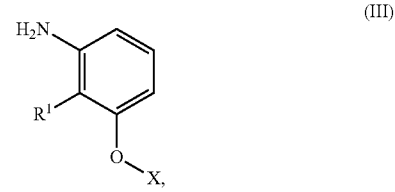

wherein $R^1$ is —CN, —C(O)OR$^2$, or —C(O)N(R$^2$)$_2$; X is alkyl, substituted alkyl, alkenyl, substituted alkenyl, heteroalkyl, substituted heteroalkyl, heteroalkenyl, or substituted heteroalkenyl; and each $R^2$ is independently hydrogen or C1-C12 alkyl.

In one embodiment, the present invention provides a compound having structural Formula (IV):

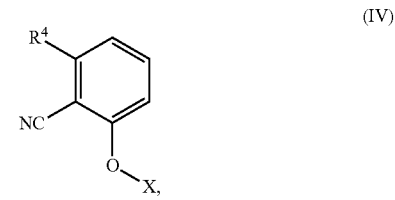

wherein $R^4$ is nitro, —NH$_2$, or halo; and X is alkyl, substituted alkyl, alkenyl, substituted alkenyl, heteroalkyl, substituted heteroalkyl, heteroalkenyl, or substituted heteroalkenyl.

In one embodiment, the present invention provides a compound having structural Formula (VII):

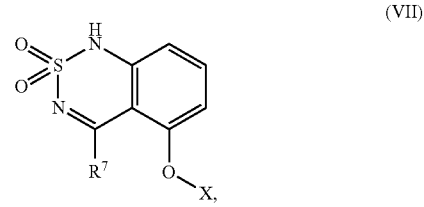

wherein X is alkyl, substituted alkyl, alkenyl, substituted alkenyl, heteroalkyl, substituted heteroalkyl, heteroalkenyl, or substituted heteroalkenyl; and $R^7$ is a leaving group selected from the group consisting of halo, -OMs, -OTs, and -OTf.

In preferred embodiments of the above described compounds, X is C1-C12 alkyl, C1-C12 heteroalkyl, C1-C12 alkenyl, C1-C12 heteroalkenyl, —Y—C(O)—OR$^2$, or —Y—C(O)—NH—R$^2$; Y is C1-C12 alkylene or C1-C12 alkenylene; and each $R^2$ is independently hydrogen or C1-C12 alkyl.

In one embodiment, the present invention provides a compound having a structural formula of $R^6$—Y—C(O)—NH—R$^2$, wherein $R^2$ is hydrogen or C1-C12 alkyl; and $R^6$ is halo or hydroxyl.

In preferred embodiments of the above described compounds, X is selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH₂CH₂CH₂CH₂CH₃, —CH₂C(CH₃)₂CH₃,
—C(CH₃)₂CH₂CH₃, —CH₂CH₂CH(CH₃)₂,
—CH₂CH₂CH₂CH₂CH₃, —CH₂C(CH₃)₂CH₂CH₃,
—CH₂CH₂C(CH₃)₂CH₃, —CH₂CH₂CH₂CH(CH₃)₂,
—CH₂CH(CH₂CH₃)CH₂CH₃, —CH₂CH₂OCH₃,
—CH₂CH₂CH₂OCH₃, —CH₂CH₂CH₂OCH₂CH₃, and
—CH₂CH₂CH₂CH₂OCH₂CH₃.

In preferred embodiments of the above described compounds, Y is selected from the group consisting of —CH₂—, —CH₂CH₂—, —CH₂CH₂CH₂—, —C(CH₃)₂—, —CH₂CH₂CH₂CH₂—, —CH₂C(CH₃)₂—, —CH₂CH₂CH₂CH₂CH₂—, —CH₂C(CH₃)₂CH₂—, —C(CH₃)₂CH₂CH₂—, —CH₂CH₂C(CH₃)₂—, —CH₂CH₂CH₂CH₂CH₂CH₂—, —CH₂C(CH₃)₂CH₂CH₂—, —CH₂CH₂C(CH₃)₂CH₂—, —CH₂CH₂CH₂C(CH₃)₂—, and —CH₂CH(CH₂CH₃)CH₂CH₂—.

Specific Embodiments

The following examples and schemes are provided to illustrate the processes/methods and intermediates for preparing compounds of the present invention.

In one embodiment of the present invention, the compound having structural formula (I) or formula (Ia) is compound 9 below:

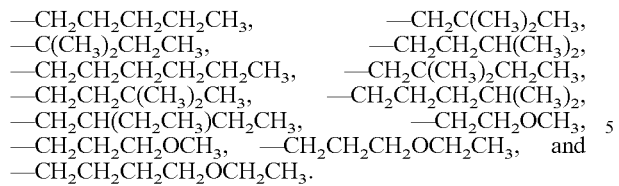

9

One approach to the synthesis of 9 (scheme 1) requires 4 steps starting from commercially available 3-hydroxy-2,2-dimethylpropanoic acid (1). The acid 1 is first coupled to the amine 2 using conventional coupling reaction to provide the amide 3 that is further reacted with 2-amino-6-fluorobenzonitrile 4 (Chimia 2006, 60, 584) to give the 2-amino nitrile derivative 5. Treatment of 5 with sulfamoyl chloride 7, prepared from chlorosulfonyl isocyanate 6 (Brodsky, B. H.; Bois, J. D. J. Am. Chem. Soc. 2005, 127, 15391), provides the sulfamoylamino derivative 8 that is further cyclized to 9 in the presence of NaOH.

Scheme 1

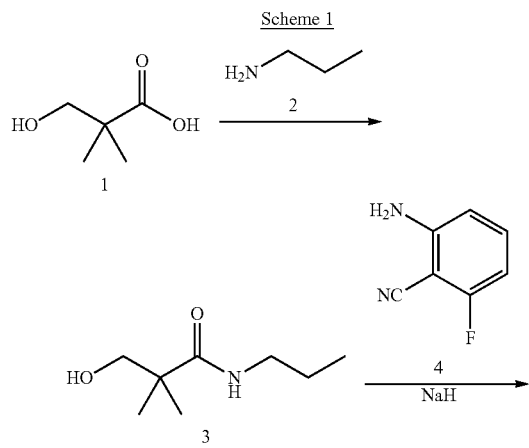

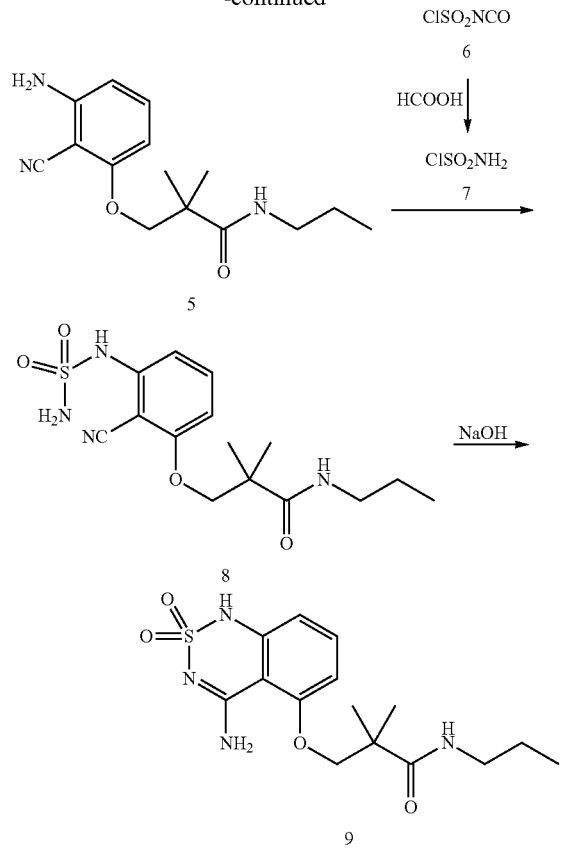

In one embodiment of Scheme 1, different bases were evaluated for the conversion of compound 3 to compound 5. These bases are NaH (60% dispersion in mineral oil), NaHMDS (1M in THF), KO'Bu (1M in THF) using THF as the solvent, and K₂CO₃ using DMF as the solvent. In one specific example, the number of equivalents of NaH was evaluated by monitoring the reaction by GC. It was determined that 1.7 equivalents of NaH was the preferred amount of base with this reaction typically being heated at reflux overnight. Work-up of the reaction was also investigated. One approach was to remove about ⅔ of the THF by distillation then dilute back to the original volume with MTBE and conduct two water washes, so that the pH of the 2$^{nd}$ wash was 10-11. Solvent swapping into EtOAc could then be done followed by concentration and precipitation with hexanes. The ratio of EtOAc to hexanes is from about 5 volumes of EtOAC to about 10 to 15 volumes of hexanes.

Due to the large amount of gas that can be instantaneously generated when reacting chlorosulfonyl isocyanate (CSI) with formic acid, an extensive safety evaluation was conducted. In one embodiment of Scheme 1, evaluation of this reaction using triethylamine as an additive was conducted, particularly under certain diluted conditions, such as e.g., CSI (1 equivalent) mixed with CH₂Cl₂ (15.6 volumes) and heated at 42° C., then added HCOOH (1.02 equivalents) containing Et₃N. Varying amounts of triethylamine were added 1, 2, 3 and 5 mol % and the rate of gas evolution was measured. It was determined that 5 mol % was the preferred amount to use as this gave a more instantaneous reaction once the initial charge of formic acid had been consumed. Different concentrations were also investigated and it was shown that the reaction could be operated successfully between 2.2 volumes of $CH_2Cl_2$ and 15.6 volumes of $CH_2Cl_2$ maintaining the equivalents of CSI and HCOOH at 1:1.02 and varying amounts of triethylamine from 1-5 mol %. Dilution of the formic acid solution with $CH_2Cl_2$ up to 1 volume was also successfully demonstrated and adopted for scale up so that a more accurate control of the amount of each aliquot added could be achieved. Since there was an initiation period being observed for the chlorosulfonyl isocyanate reaction, a method for determining when the 1$^{st}$ aliquot had completely reacted was required so as to avoid any potential accumulation which could have adverse safety consequences. After the 1$^{st}$ aliquot is consumed gas evolution could easily be observed by foaming of the reaction mixture along with a noticeable endotherm. A reaction was run looking at different ways of monitoring the reaction. In the laboratory the ReactIR appeared to be a plausible tool for monitoring the reaction. Other methods investigated include FTIR and direct injection mass spectroscopy. Another method involved taking a sample of the gas and injecting it on the GC (using a TCD detector) looking for CO and $CO_2$. Since a standard of $CO_2$ was readily at hand this was injected and $CO_2$ gas evolution was confirmed with another peak being seen which was believed to be CO. This GC method was then further evaluated by carrying out the reaction with a constant $N_2$ flow. In summary, the reaction of chlorosulfonyl isocyanate with formic acid could be monitored avoiding any accumulation and the adverse consequences thereof.

In one embodiment of Scheme 1, the reaction of converting compound 5 to compound 8 was conducted using a solvent selected from methylene chloride, a mixture of methylene chloride and dimethylacetamide, a mixture of methylene chloride and acetonitrile, or a combination thereof. For example, a mixture of methylene chloride and dimethylacetamide with the volume ratio of 8 to 0.5 was used as a solvent for the reaction. In another example, acetonitrile was added to the methylene chloride solution of compound 7 prior to mixing the solution of compound 7 with the solution of compound 5. The mixing process could be carried out by either adding compound 7 to compound 5 or adding compound 5 to compound 7. In one example, after the reaction was finished, the reaction mixture was quenched with saturated $NaHCO_3$ solution. After quenching with saturated $NaHCO_3$ solution, compound 8 was extracted from the $CH_2Cl_2$ solution using 5 equivalents of a 1N NaOH solution followed by a back extraction of the organic layer with 0.67 equivalents of a 1N NaOH solution. This gave a solution of compound 8 in aqueous NaOH.

In one embodiment of Scheme 1, the cyclization of compound 8 was performed under aqueous conditions. Preferably, the NaOH solution of compound 8 was washed with MTBE prior to the cyclization reaction. Various temperatures (r.t., 45° C., 65° C. and 80° C.) were investigated for the cyclization. In one example, the cyclization was carried out by first washing the NaOH solution of compound 8 with MTBE, which was followed by addition of EtOH and then acidification with HCl to precipitate compound 9. The reaction yield and purity of compound 9 based on the solid precipitates could be adjusted by adding different amounts of EtOH. Then, purification of the precipitates (crude compound 9) was investigated. The preferred approach was to slurry the crude material in a 50:50 mixture of EtOH/water at 80° C. for 2 hours and then cool to ambient temperature, filter and wash.

As shown by Scheme 2 below, commercially available methyl 3-hydroxy-2,2-dimethylpropanoate (10) can be easily converted to amide 3 by treatment with neat amine 2 at elevated temperatures and/or pressurized condition. In one embodiment, preparation of compound 3 from compounds 1 and 2 is conducted at a pressurized condition. Experiments were conducted using a 300 mL Parr reactor to evaluate the reaction at a temperature lower than 200° C. Initial conditions of pressurizing the reactor to 400 psig with nitrogen and then heating it to 120° C. gave complete conversion within 24 h. The pressure generated when operating under these conditions exceeded 600 psig which was above what the 5-Gal reactor can currently operate at safely, given the rating of the vent lines (this being not greater than 500 psig total). A variety of conditions for the pressure reaction of methyl 3-hydroxy-2,2-dimethylpropanoate 1 with n-propylamine 2 (1 or 1.5 equivalents) were then investigated with and without pressurizing the reactor with nitrogen. One of the preferred reaction conditions was to run the reaction at 120° C. without any additional nitrogen pressure using 1.5 equivalents of n-propylamine. Concentration of this material using toluene as a solvent to azeotropically remove the methanol by-product, as well as the excess n-propylamine was then conducted. This gave 3 as a viscous oil which was typically used as is, but it was observed that upon standing, this material would begin to crystallize.

Scheme 2

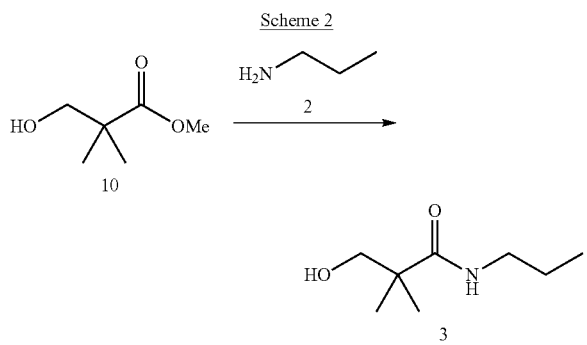

Other methods can be used to improve the synthesis of the amide 3 to obtain a process that is scalable (for a review see Tetrahedron 61 (2005) 10827-10852). This includes the use of other coupling reagents, other esters or the use of an activated carboxylic acid 1, such as, for example, acyl chloride or fluoride 1a, mixed anhydride 1b, ethoxy vinylester 1c, acyloxyboronate 1d (Scheme 3).

Scheme 3

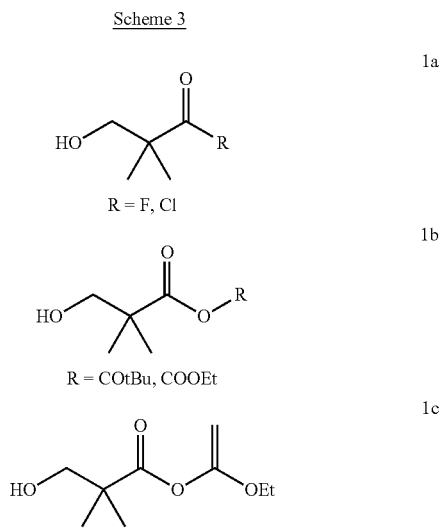

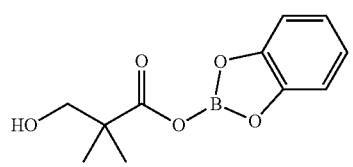

1d

The amide 3 can also be reacted with 2,4-dinitrobenzonitrile 11 using NaH, potassium tert-butoxide or other suitable bases in THF, DMF or other appropriate solvents (N. V. Harris, C. Smith, K. Bowden, J. Med. Chem. 1990, 33, 434) to provide the intermediate 12 that is further reduced to the desired intermediates 5 by hydrogenation in the presence of Pd/C or other reducing agents (Scheme 4).

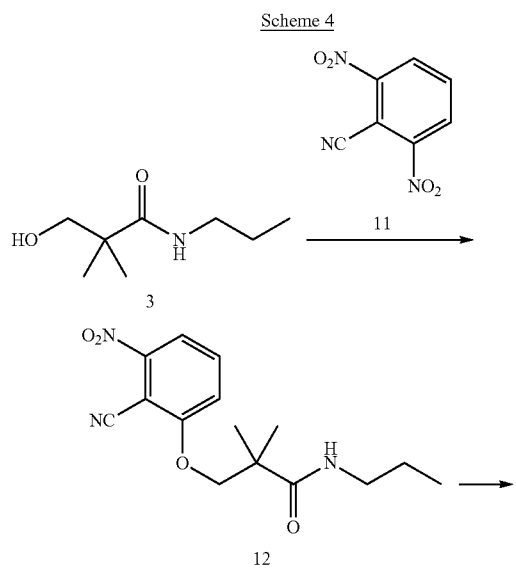

Alternatively, the amide 12 can be prepared from the acid 1 or the ester 10, by first reaction with nitro benzene 11 to provide the intermediates 13 and 14, respectively. The ester 14 can be further hydrolyzed to the acid 13, and then the acid 13 is coupled to the amine 2 to provide the amide 12 (Scheme 5). Other esters can be used instead of the methyl ester including other alkyl esters, such as ethyl, butyl, tert-butyl to improve the hydrolysis process.

Scheme 5

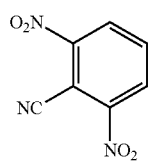
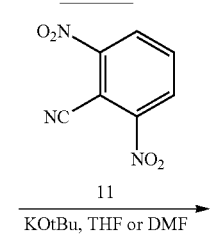

As shown in Scheme 6, 3'-(3-amino-2-cyanophenoxy)-2',2'-dimethyl-N-propylpropanamide 5 can be prepared from another route by reacting the alcohol 3 with 2,6-difluorobenzonitrile 15 (J. Thurmond et al, J. Med. Chem. 2008, 51, 449) to provide the fluoro derivative 16 that can be further reacted with ammonia to provide the desired intermediate 5.

Scheme 6

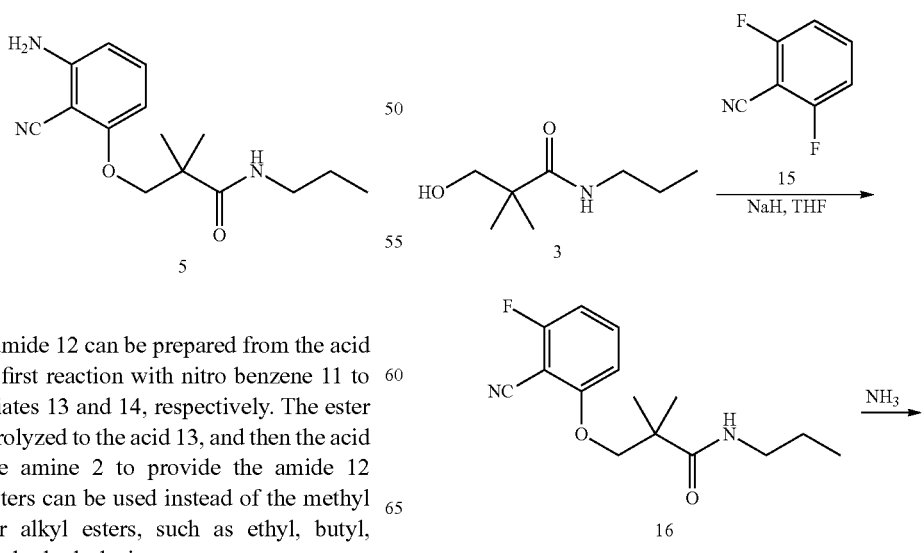

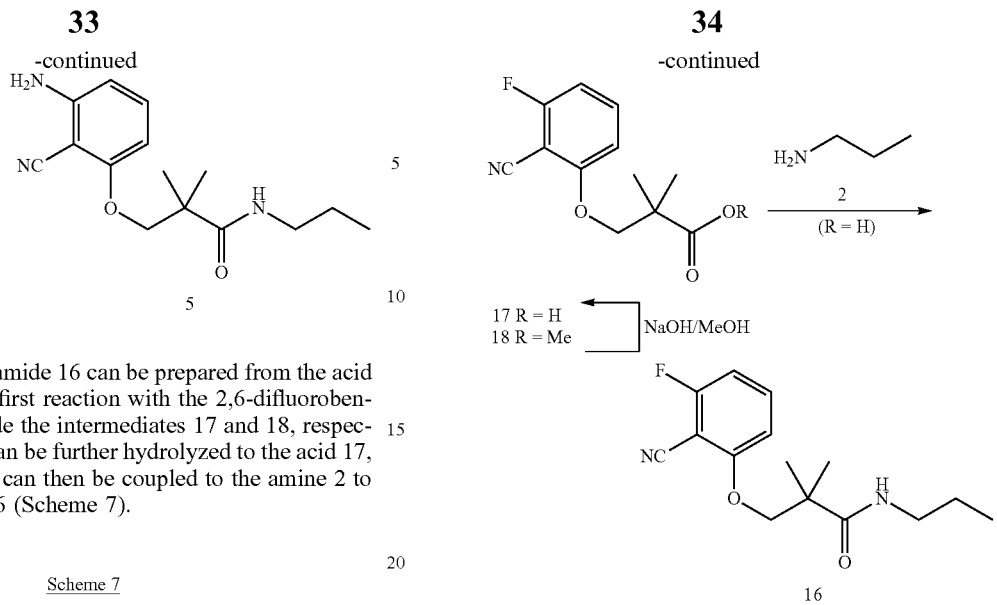

Alternatively, the amide 16 can be prepared from the acid 1 or the ester 10 by first reaction with the 2,6-difluorobenzonitrile 15 to provide the intermediates 17 and 18, respectively. The ester 18 can be further hydrolyzed to the acid 17, and then the acid 17 can then be coupled to the amine 2 to provide the amide 16 (Scheme 7).

Another alternative to the synthesis of intermediate 5 is described in Scheme 8. The acid 1 or ester 10 is reacted with 2-amino-6-fluorobenzonitrile 4 to provide the acid 19 or the ester 20, respectively. The later can be alternatively prepared from the intermediates 13 and 14, respectively, by reduction of the nitro group to the amino group using for example $SnCl_2$ or other appropriate known reducing agents. The acid 19 or the ester 20 can then be converted using the usual procedures described above to the amide 5.

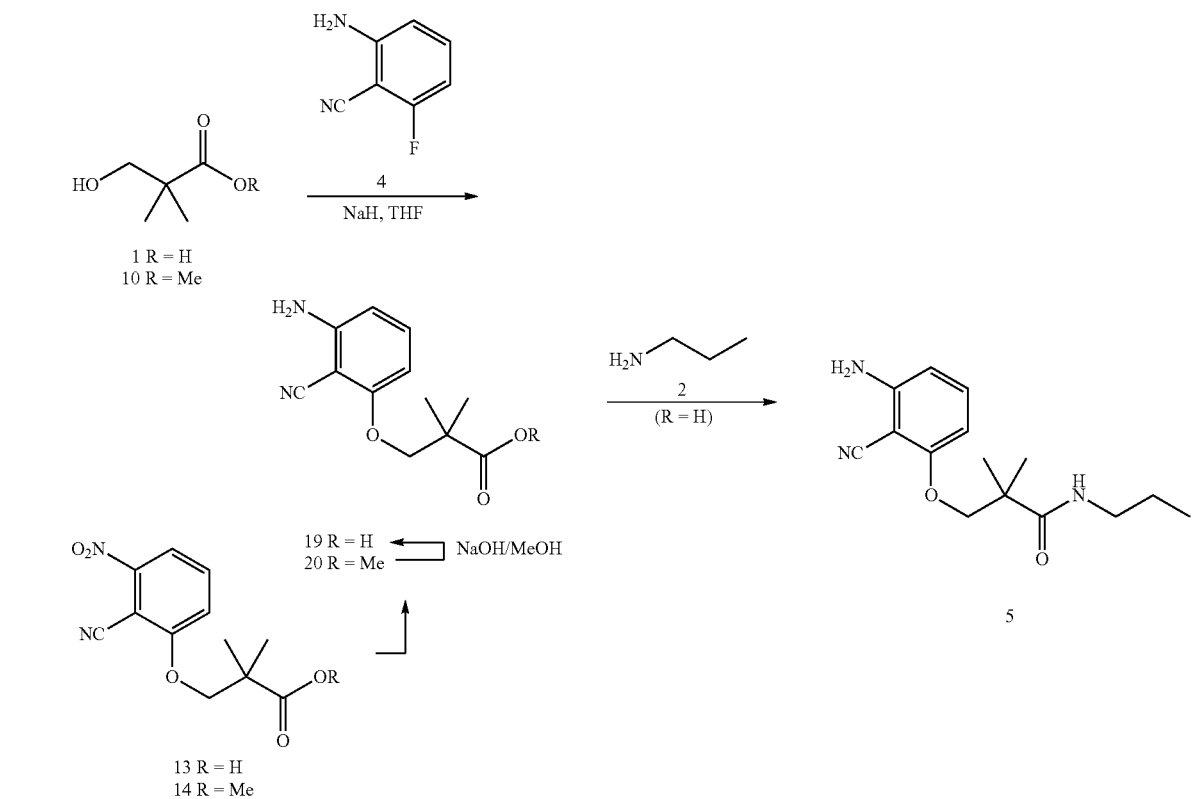

Commercially available 2-fluoro-6-nitrobenzonitrile 21 (N. Gueduira, R. Beugelmans, J. Org. Chem. 1992, 57, 5577-5585) can also be treated with the alcohols 1, 10 or 3 to provide respectively the desired intermediates 13, 14 and 12 (Scheme 9) that can be further converted to 5 using procedures as described above.

Scheme 9

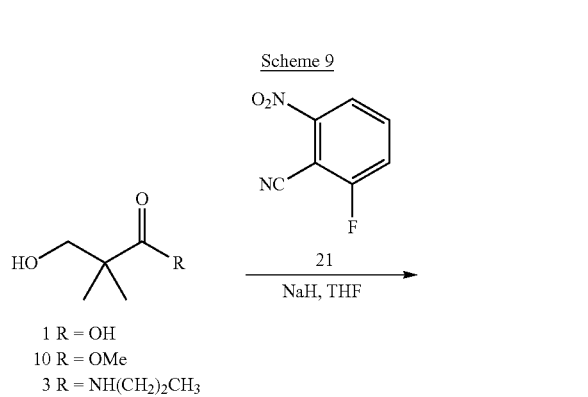

Other approaches involve the alkylation of commercially available phenols 22 or 23 with bromo derivatives 24, 25 or 26 to provide intermediates 13, 14, 12, 17, 18 or 16 that can be converted to 5 using procedures as described above. The bromo derivative 24 is commercially available. Compounds 25 and 26 can be prepared using conventional methods from 10, 24 or 3 as shown in Scheme 10 bellow. Bromo derivatives 24, 25, and 26 can be replaced with chloro, iodo, mesylate, tosylate analogs that are synthesized using known methods from the corresponding alcohols.

Scheme 10

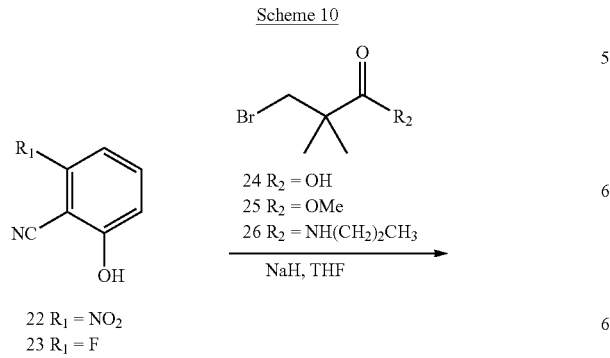

13 $R_1$ = $NO_2$ $R_2$ = OH
14 $R_1$ = $NO_2$ $R_2$ = OMe
12 $R_1$ = $NO_2$ $R_2$ = $NH(CH_2)_2CH_3$
17 $R_1$ = F $R_2$ = OH
18 $R_1$ = F $R_2$ = OMe
16 $R_1$ = F $R_2$ = $NH(CH_2)_2CH_3$

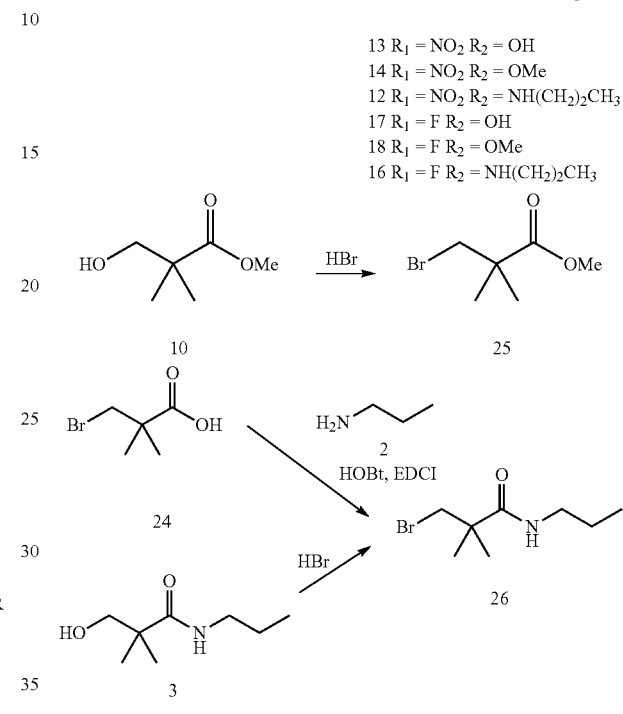

As shown in Scheme 11 below, Mitsunobu reaction can also be used to introduce the side chain by reacting the phenols 22 or 23 with the alcohols 10 or 3 to produce the desired derivatives 12, 14, 16 or 18.

Scheme 11

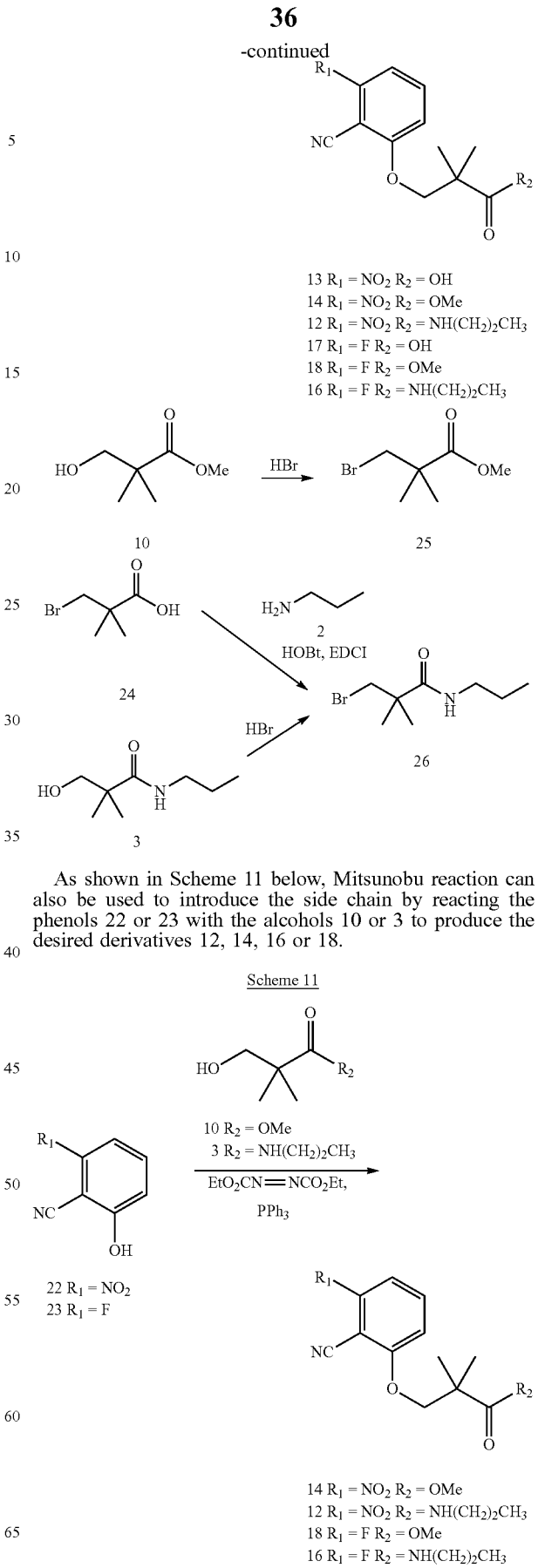

As shown in Scheme 12 below, 2-amino nitrile 5 can be converted in one step to 3'-(4-amino-2,2-dioxide-1H-benzo[c][1,2,6]thiadiazin-5-yloxy)-2',2'-dimethyl-N-propylpropanamide, i.e., compound 9 by treatment with sulfonamide 27 in presence of DBU at elevated temperature or in a two steps process via its reaction with sulfamoyl chloride 7 to provide the intermediate 8 that is further cyclized to 9 in the presence of NaOH (Marayanoff et al, *J. Med. Chem.* 2006, 49, 3496 and references cited therein).

Scheme 12

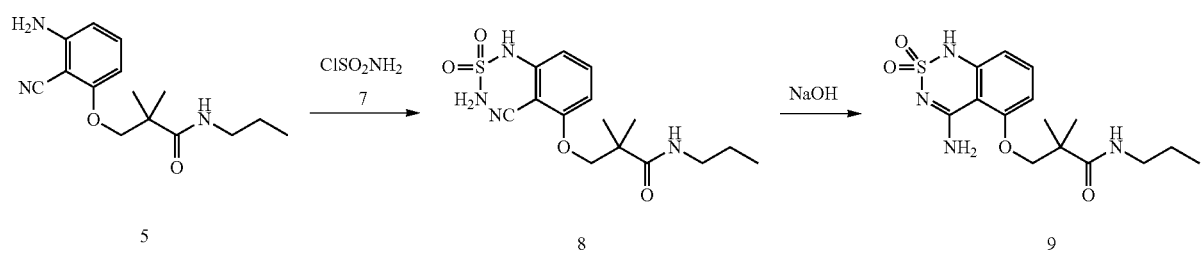

Alternatively (Scheme 13), 2-amino nitriles 19 and 20 can be converted in one step by treatment with sulfonamide 27 in presence of DBU at elevated temperature to provide 1H-benzo[c][1,2,6]thiadiazin-5-yloxy) derivative 30 that can be further reacted with amine 2 to provide the amide 9. Amino nitriles 19 and 20 can also be converted to the cyclized derivative 30 in two steps via the sulfonamides 28 and 29, respectively.

Scheme 13

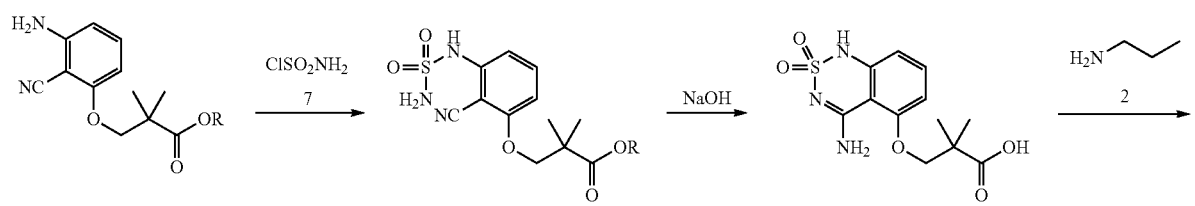

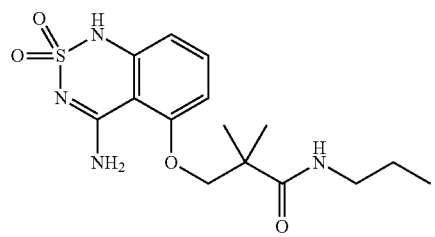

Alternative approaches to the preparation of useful intermediates in the synthesis of compound 9 are described in Scheme 14, 15, and 16.

As shown in Scheme 14, amino nitriles 19, 20 and 5 can be converted to corresponding amino amides derivatives by hydrolysis of the nitrile group. These intermediates can be further reacted with sulfamoyl chloride to provide the sulfamides 34, 35 or 36 that can be cyclized using a variety of reagents such as EDCI (Chem. Pharm. Bull. 2004, 52, 1422) or $P_2O_5$ to produce respectively 30, 37 or 9.

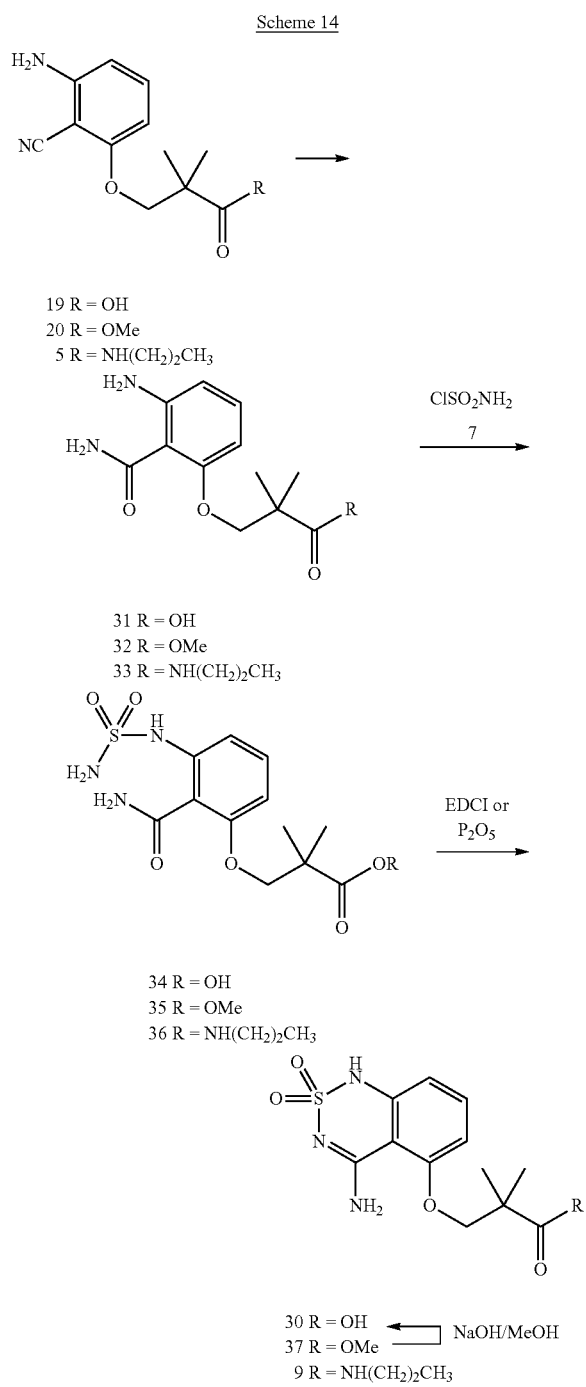

ing cyclized 1H-benzo[c][1,2,6]thiadiazin-4-ols 38, 39 and 40. The hydroxyl can be converted to a leaving group X (X=Cl, OMs, OTs, OTf) using conventional methods to provide intermediates 41, 42 or 43, that can be displaced with ammonia (Bioorg. Med. Chem. Lett. 2005, 15, 3853) to provide the corresponding 1H-benzo[c][1,2,6]thiadiazin-4-amines 30, 37 or 9.

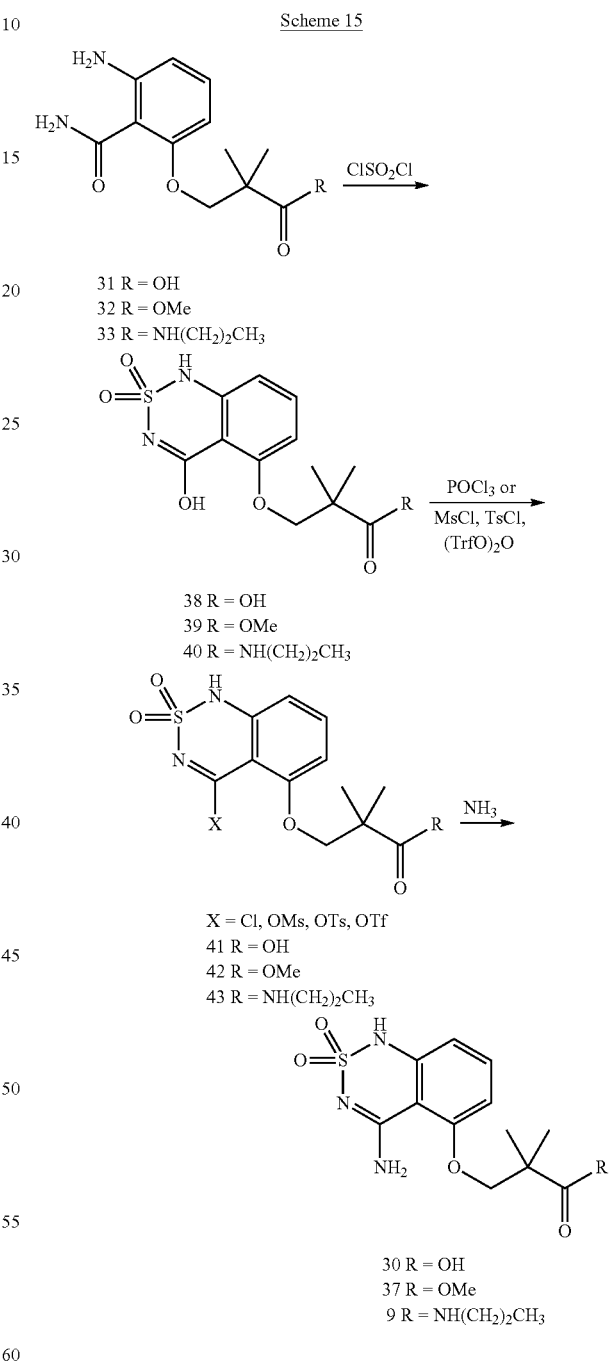

As shown in Scheme 15, amino amides 31, 32 and 33 can be reacted with sulfonyl chloride to provide the correspond- Another approach is described in Scheme 16. Commercially available 2,6-dinitrobenzoic acid 44 can be reacted with alcohol 3 to provide the nitro benzoic acid 45 that can be converted to the corresponding methyl ester (or other appropriate ester) to give 46. The nitro group can be reduced to the amino group using conventional method (for example reduction in the presence of $SnCl_2$) and the ester 47 treated with ammonia to provide the desired intermediate 33. Alternatively, the carboxylic acid 45 can be reacted with sulfonyl chloride (to provide the acyl chloride) and then with ammonia to provide 48 that is further hydrogenated to give the desired intermediate 33.

further cyclized to 53 in the presence of NaOH. The synthesis can be done in a 2 steps process by reacting the intermediate 51 with sulfamide 27 in the presence of DBU or other suitable base at elevated temperature to provide directly the cyclized 53.

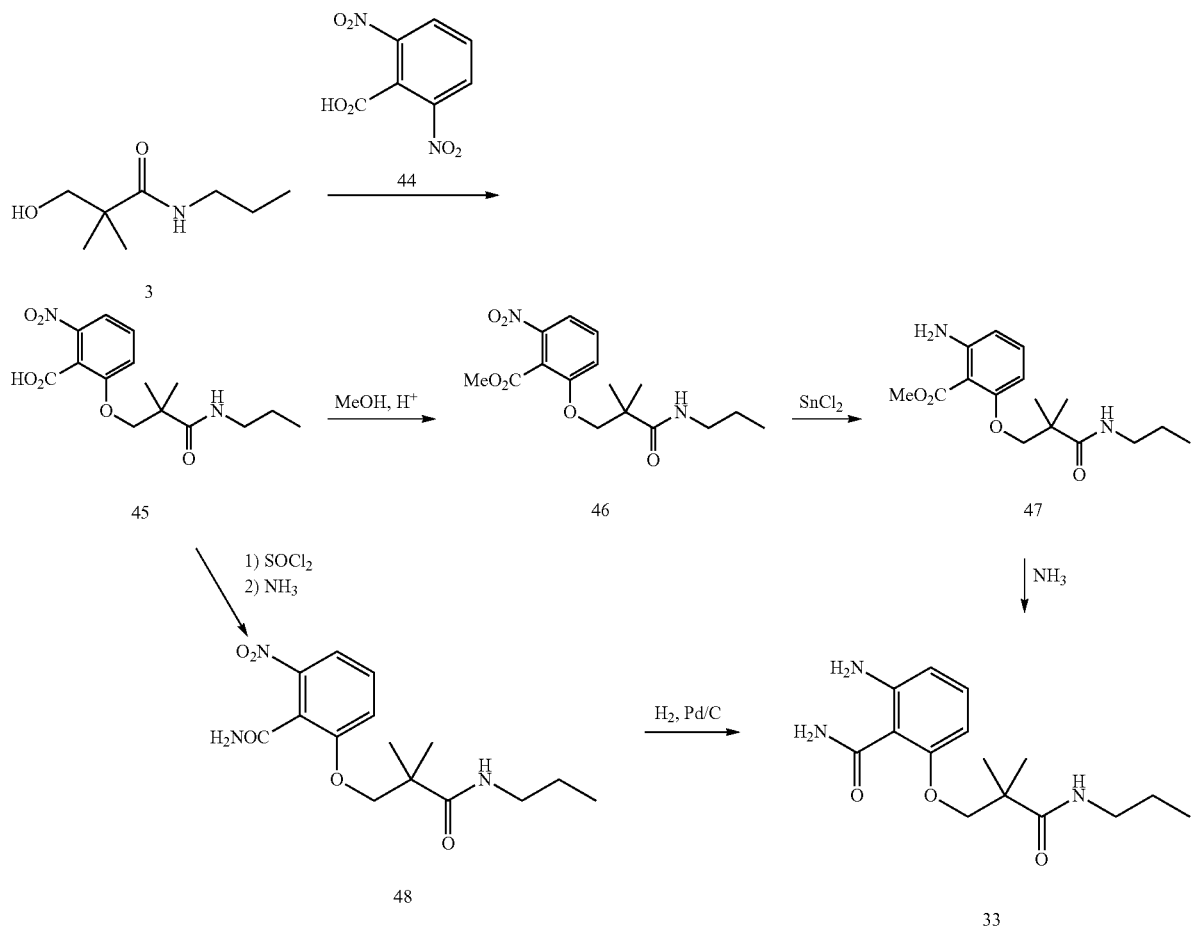

In one embodiment of the present invention, the compound having structural Formula (I) is compound 53 below:

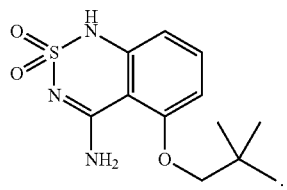

One approach to the synthesis of compound 53 (scheme 17) requires 3 steps starting from commercially available 2,2-dimethylpropan-1-ol 50 that is first reacted with 4 to provide the intermediate 51. Treatment of 51 with sulfamoyl chloride 7 provide the sulfamoylamino derivative 52 that is

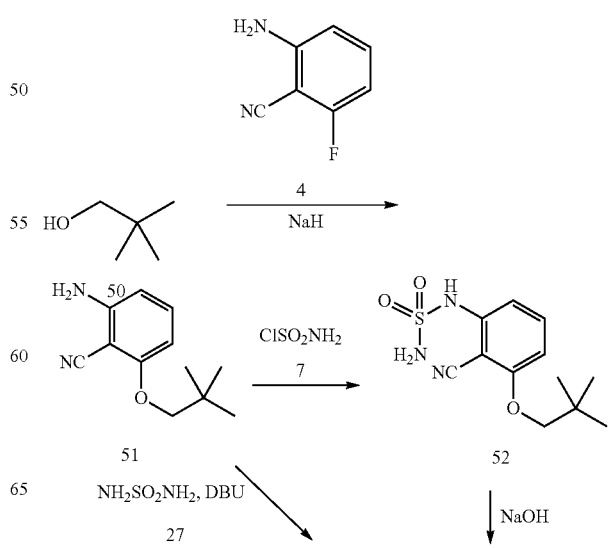

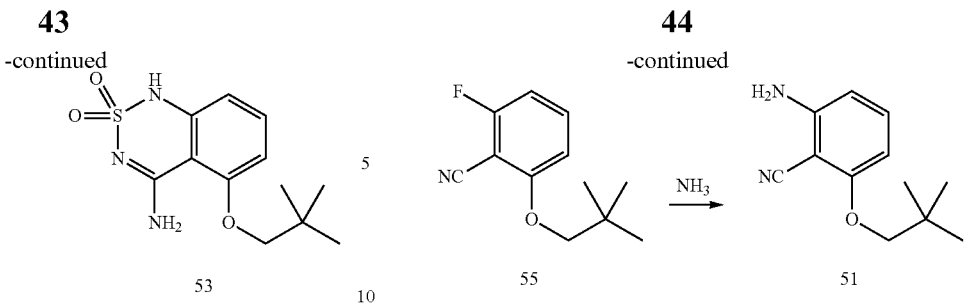

As shown in Scheme 18, the alcohol 50 can also be reacted with commercially available 2,4-dinitrobenzonitrile 11 (N. V. Harris, C. Smith, K. Bowden, J. Med. Chem. 1990, 33, 434) or 2-fluoro-6-nitrobenzonitrile 21 to provide the intermediate 54 that is further reduced to the desired intermediates 51 by hydrogenation in the presence of Pd/C or other reducing agents.

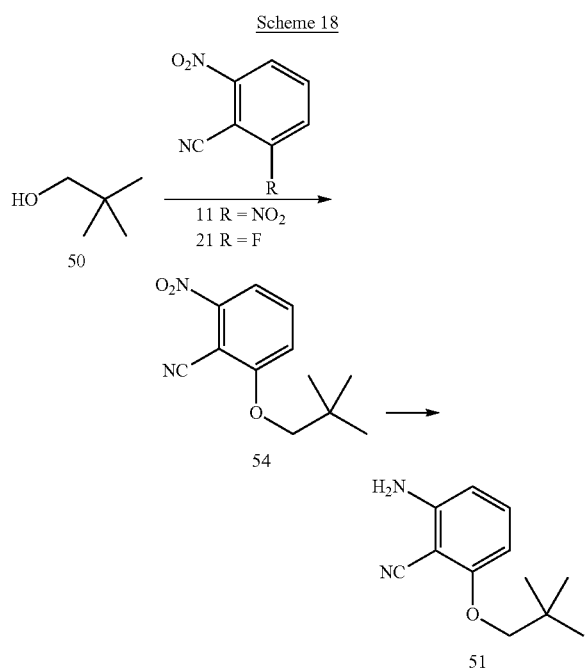

As shown in Scheme 19, 3'-(3-amino-2-cyanophenoxy)-2',2'-dimethyl-propane 51 can be prepared from another route by reacting the alcohol 50 with 2,6-difluorobenzonitrile 15 (J. Thurmond et al, J. Med. Chem. 2008, 51, 449) to provide the fluoro derivative 55 that can be further reacted with ammonia to provide the desired intermediate 51.

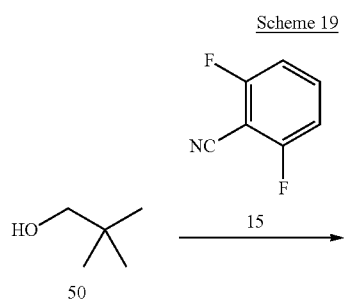

Another approach (as shown in Scheme 20) involves the alkylation of commercially available phenols 22 or 23 with commercially available 1-bromo-2,2-dimethylpropane 56, 1-chloro-2,2-dimethylpropane 57 or 1-iodo-2,2-dimethylpropane 58 to provide intermediates 54 and 55 that can be converted to 51 using procedures as described above. Bromo 56, Chloro 57 and Iodo 58 can be replaced with mesylate or tosylate analogs that are synthesized using known methods from the corresponding alcohols. Mitsunobu reaction can also be used to introduce the side chain by reacting the phenols 22 or 23 with the alcohol 50.

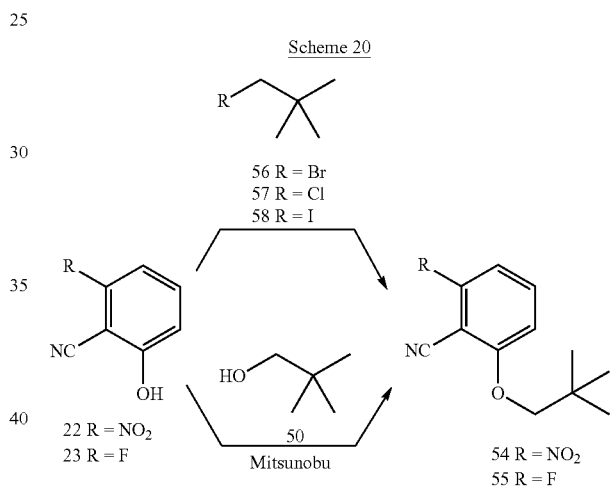

Alternates approaches to the preparation of useful intermediates in the synthesis of compound 53 are described in Schemes 21, 22, and 23.

As shown in Scheme 21, amino nitrile 51 can be converted to its corresponding amino amide derivative 59 by hydrolysis of the nitrile group. This intermediate 59 can be further reacted with sulfamoyl chloride to provide the sulfamide 60 that can be cyclized using a variety of reagents such as EDCI or $P_2O_5$ to produce 53.

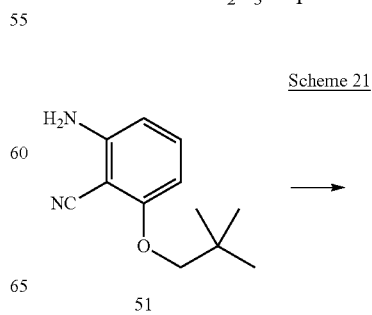

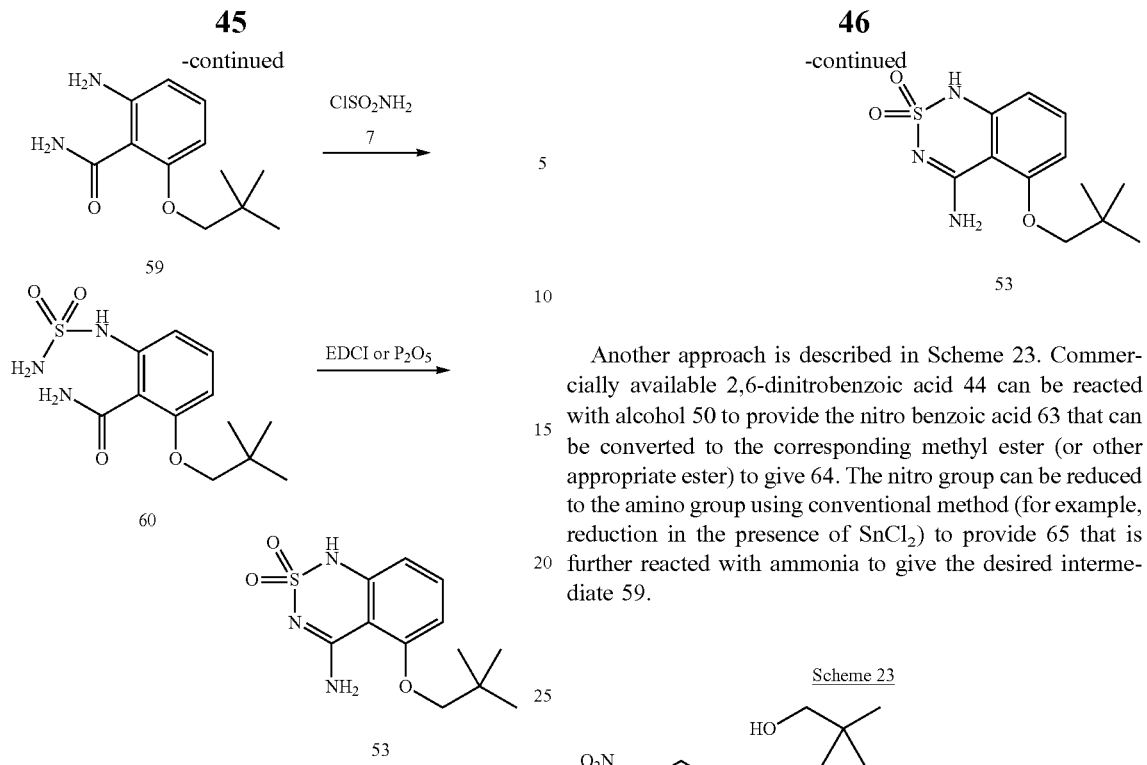

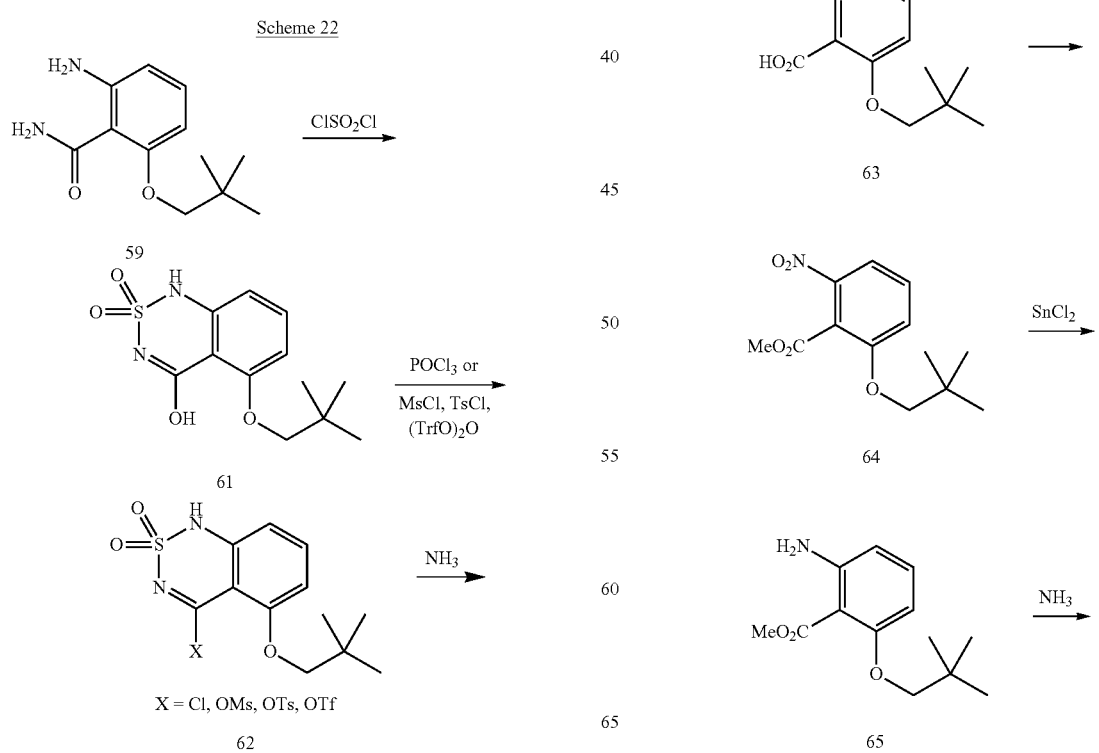

Another approach is described in Scheme 23. Commercially available 2,6-dinitrobenzoic acid 44 can be reacted with alcohol 50 to provide the nitro benzoic acid 63 that can be converted to the corresponding methyl ester (or other appropriate ester) to give 64. The nitro group can be reduced to the amino group using conventional method (for example, reduction in the presence of $SnCl_2$) to provide 65 that is further reacted with ammonia to give the desired intermediate 59.

Alternatively, as shown in Scheme 22, amino amide 59 can be reacted with sulfonyl chloride to provide the corresponding cyclized 1H-benzo[c][1,2,6]thiadiazin-4-ol 61. The hydroxyl can be converted to a leaving group X (X=Cl, OMs, OTs, OTf) using conventional methods to provide intermediate 62. The leaving group can be can be displaced with ammonia to provide compound 53.

-continued

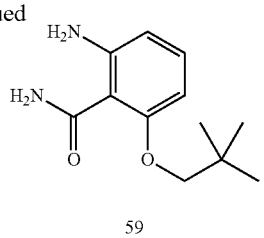

59

In one embodiment of the present invention, the sodium salt of compounds 9 or 53 can be prepared by reacting 9 or 53 with NaOH, NaHCO$_3$, or Na$_2$CO$_3$ (Scheme 24). Other suitable salts can also be made using appropriate procedures, such as Potassium, Calcium and Magnesium salts. The salts form of the compounds have better solubility in aqueous solution as well as in polyglycol and other solvents that are used to make stock solutions for food applications.

Scheme 24

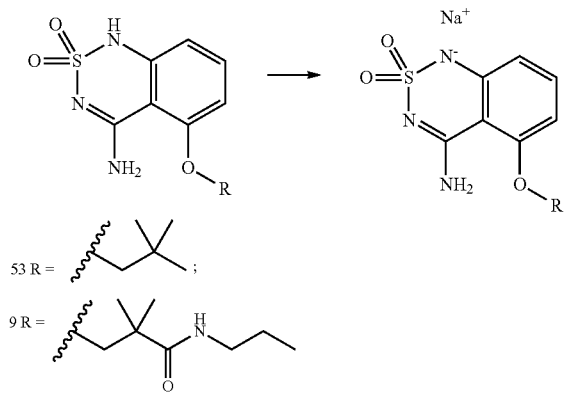

EXAMPLES

GC Conditions

Agilent GC with an Agilent HP-5 column, 30 m (L)×0.32 mm (ID)×0.25 µm (df)

| | |
|---|---|
| Inlet | Split; Split Ratio 100:1 |
| Inlet Temperature | 300° C. |
| Inlet Pressure | 10.0 psi (constant pressure) |
| Thermal Program | Initial 50° C. (hold for 0.70 min) |
| | Ramp to 300° C. (hold 5 min) |
| | at 30° C./min |
| Detection | Flame Ionization |
| Detector Temperature | 320° C. |
| Carrier Gas | Helium |
| Makeup Gas | Helium, 35 mL/min |
| Air Flow | 350 mL/min |
| Hydrogen Flow | 40 mL/min |
| Injection Volume | 1 µL |
| Run Time | 14.03 min |
| Diluent | Compound 1 and Compound 2 (methanol) |
| | Compound 3 (acetonitrile) |
| | Approximate Retention Time, min |
| Compound 1 | 3.690 |
| Compound 2 | 6.062 |
| 2-Amino-6-fluorobenzonitrile | 6.099 |
| Compound 3 | 10.874 |

HPLC Conditions

Agilent HPLC with a Waters J'sphere ODS-H80 C18 column, 4-µm particle size, 4.6 mm×150 mm

| | |
|---|---|
| Flow rate | 1.0 mL/min |
| Detection | UV at 230 nm |
| Column Temperature | 25° C. |
| Injection Volume | 1 µL |
| Run Time | 30 min |
| Mobile Phase A | 0.1% formic acid in DI water |
| Mobile Phase B | 0.1% formic acid in acetonitrile |
| Diluent | 1:0.5:0.5 formic acid:acetonitrile:DI water |

| Time (min) | (%) Mobile Phase A | (%) Mobile Phase B |
|---|---|---|
| 0.0 | 95.0 | 5.0 |
| 20.0 | 5.0 | 95.0 |
| 25.0 | 5.0 | 95.0 |
| 27.0 | 95.0 | 5.0 |
| 30.0 | 95.0 | 5.0 |

| | Approximate Retention Time, min |
|---|---|
| Compound 3 | 11.7 |
| Compound 3a | 10.0 |
| Compound 4 | 9.4 |

Example 1. Synthesis of Compound 3

To a 5-Gal pressure reactor was charged methyl 3-hydroxy-2,2-dimethylpropanoate 10 (4.5 kg, 34.05 mol, 1 equiv.) and n-propylamine 2 (3.02 kg, 4.2 L, 51.07 mol, 1.5 equiv.) and the mixture stirred and heated to 120° C. The pressure of the reactor rose to 54 psig and the temperature of the reactor was maintained by the use of a heating jacket and internal cooling coils that contained glycol. This setup did cause the internal pressure to fluctuate over a range of 30 psig to 54 psig due to the cooling and heating of the vapor phase of the reactor. The reaction was monitored by GC and after 93 h the residual methyl 3-hydroxy-2,2-dimethylpropanoate 1 was 1.95% (AUC) by GC relative to compound 3. The contents of the reactor were then allowed to cool to ambient temperature and the batch was transferred to a suitable container and concentrated on a 20-L rotary evaporator using toluene to azeotropically remove residual methanol along with the low boiling n-propylamine. This gave compound 3 (5.65 kg, 86% (AUC by GC) as a concentrate which had a high level of residual n-propylamine (~3.44%) and was stored for combination with a 2$^{nd}$ batch and observed to solidify on standing.

A 2$^{nd}$ batch was processed in a similar manner at the same scale to give compound 3 (5.267 kg, 86% (AUC) by GC) as a concentrate containing ~4% n-propylamine. A use test of compound 3 that contained ~4.3% n-propylamine was conducted through to compound 5 and confirmed that this high level of residual n-propylamine did not affect the quality of the material produced.

Both of these batches were dissolved in anhydrous THF for subsequent use in the next step.

Example 2. Synthesis of Compound 5

To a dried 750-L reactor purged with nitrogen was charged NaH (60% dispersion in mineral oil, 3.6 kg, 90.0 mol, 1.7 equiv.) and low water THF (160 L) and the resulting slurry was cooled to 0-10° C. Compound 3 (9.07 kg (theoretical based on wt % calculation of solutions), 57 mol, 1.08 equiv. in anhydrous THF) was then further diluted with low water THF (71 L) and charged portionwise to the NaH/THF slurry maintaining the reaction temperature at 0-10° C. Once the addition was complete the reactor was warmed to 20-25° C. and held at this temperature for at least 30 min. To this was slowly charged a solution of 2-amino-6-fluorobenzonitrile (7.2 kg, 52.9 mol, 1 equiv.) 4 in low water THF (35.5 L) over a period of at least 30 min., maintaining the reaction temperature at 20-30° C. Once the addition was complete the reaction mixture was heated to reflux and after 10 h the residual 2-amino-6-fluorobenzonitrile was 1.7% (AUC) by GC relative to Compound 5. The batch was concentrated to ~⅓ volume (to ~90 L) under partial vacuum distillation and diluted with MTBE (190 L) and washed with water (2×143 L). A sample of the organic layer was taken and tested for residual fluoride and it was found to be at a concentration of 11.6 ppm. Since the fluoride number was higher than a concentration of 5 ppm, a level at which had been deemed safe to operate at, a further water wash (143 L) was conducted along with a filtration through a 25 micron filter to remove black particles that were observed in the batch. Measurement of the residual fluoride was then repeated and determined to be at a concentration of 2.8 ppm and the organic layer was concentrated to ~⅓ volume (to ~90 L) under vacuum. The batch was diluted with EtOAc (190 L) and the process repeated, concentrating to ~⅓ volume (to ~90 L). The EtOAc dilution (190 L) and concentration was repeated to ~90 L and the batch was cooled to 20-25° C. The resulting mixture was stirred at this temperature until crystallization was observed at which point hexane (285 L) was added. The batch was further cooled to 15-25° C. and stirred at this temperature for at least 2 h before filtering and washing with hexane (2×35.5 L). The product was dried under vacuum at 50° C. for 45.75 h to give Compound 5 as a white to off-white solid (10.15 kg, 70% yield) with a purity of 97% (AUC) by GC.

Example 3. Conversion of Compound 5 to Compound 9

To a dry 750-L reactor purged with nitrogen was charged $CH_2Cl_2$ (95 L), chlorosulfonyl isocyanate 6 (9.0 kg, 63.6 mol, 2.19 equiv.) and triethylamine (161 g, 1.59 mol, 2.5 mol %) and the mixture was heated to 36-42° C. In a container was mixed 99% formic acid (3.0 kg, 65.17 mol, 1.02 equiv), $CH_2Cl_2$ (4.75 L) and triethylamine (161 g, 1.59 mol, 2.5 mol %). With a nitrogen sweep of the headspace being employed ~10% aliquots of the formic acid/triethylamine solution were added to the chlorosulfonyl isocyanate (CSI) mixture. Samples of the gas were taken periodically after addition of the $1^{st}$ aliquot to confirm $CO_2$ gas formation and cessation and once $CO_2$ gas evolution had decreased the next aliquot was added. Subsequent monitoring of the reaction of each aliquot could now easily be monitored visually by both foaming in the reactor and a noticeable decrease in the reaction temperature (~3-4° C. per 10% aliquot). Once foaming had ceased and the batch had returned to its original temperature the next aliquot could be safely added. Upon addition of the final aliquot and observed cessation of foaming and endotherming of the reaction, further gas samples were taken to confirm that $CO_2$ generation had ceased during the 60-90 minute hold period. Although $CO_2$ was still detected at low levels, two consecutive readings gave similar results and this was believed to be due to the nitrogen sweeping through the headspace of the reactor which was not efficiently displacing all the $CO_2$ present in the reactor. This process transformed compound 6 to compound 7.

The mixture containing compound 7 was then cooled to 0-10° C. and diluted with MeCN (40 L) and stirred at this temperature for 30-45 min. To the secondary 750-L reactor was charged Compound 5 (8.0 kg, 29.05 mol, 1 equiv.), $CH_2Cl_2$ (90 L) and dimethylacetamide (4 L) and was stirred until a solution was formed before cooling to 0-10° C. To this was then added the solution of sulfamoyl chloride 7 in the primary reactor over a period of 1-3 h maintaining the reactor temperature at 0-10° C. After the addition was complete the batch was allowed to warm to 20-25° C. and stirred at this temperature overnight. The reaction was monitored by HPLC and after 10.33 h the reaction was deemed complete with 10% (AUC) compound 5 remaining by HPLC relative to compound 8. The mixture was slowly quenched onto a solution of $NaHCO_3$ (10.8 kg, 128.6 mol) in water (110 L) over at least 1 h maintaining the reaction temperature at 10-30° C. The layers were allowed to separate and the aqueous layer was back extracted with $CH_2Cl_2$ (2×40 L). The combined organics were then extracted with a solution of 50% NaOH (11.6 kg, 145 mol, 5 equiv.) in water (137.6 kg) followed by 50% NaOH (1.55 kg, 19.38 mol, 0.67 equiv.) in water (18.35 kg). The combined aqueous extracts were heated at 40-50° C. for ~10 h followed by heating to 60-70° C. and holding at this temperature for ~4 h until reaction completion was observed (<1% (AUC) Compound 8 vs Compound 9 by HPLC).

The reaction mixture was cooled to 20-25° C. and washed with MTBE (2×60 L) before filtering through a 0.45 micron filter to remove any residual particles. To the aqueous solution was then charged EtOH (190 proof, 96 L) and the batch was cooled to 0-10° C. To this solution was slowly transferred a solution of 37% HCl (17.86 kg) in water (30 L) over a period of at least 30 min. until the pH of the reaction mixture was ~4.5. At this point the batch had precipitated and was held at 0-10° C. for a minimum of 1 h before filtering and washing with DI water (2×25 L) followed by a 2:1 mixture of DI water/EtOH (25 L). The batch was dried under vacuum at 40-50° C. for 40 h to give crude Compound 4 as a pale yellow solid (6.8 kg, 66% yield from Compound 5) with a purity of 93.2% (AUC) by HPLC.

Example 4. Purification of Compound 9

To the 750-L reactor was charged crude compound 9 (6.8 kg), EtOH (190 proof, 68 L) and DI water (68 L). The resulting slurry was heated to 75-85° C. and held at this temperature for 2 h before cooling to 15-25° C. overnight (~16 h). The slurry was filtered and washed with a 2:1 mixture of DI water/EtOH (28.4 L). The batch was dried under vacuum at 40-50° C. for ~15 h to give compound 9 as an off-white solid (6.4 kg, 94% recovery) which contained ~0.3% (AUC) compound 5 by HPLC.

The batch was reworked in an identical manor with the solvent amounts and wash volumes remaining unchanged. This gave compound 9 as a white solid (5.83 kg, 57% yield from compound 5) with a purity of 99.9% (AUC) and 0.03% (AUC) compound 5 by HPLC.

All publications and patent applications referenced herein are incorporated by reference to the same extent as if each individual publication or patent application was specifically and individually indicated to be incorporated by reference.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

What is claimed is:

1. A compound having structural Formula (II)

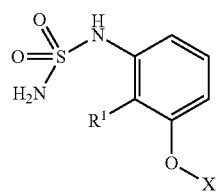

wherein
R¹ is —CN, —C(O)OR², or —C(O)NH₂;
X is alkyl, substituted alkyl, alkenyl, substituted alkenyl, heteroalkyl, substituted heteroalkyl, heteroalkenyl, or substituted heteroalkenyl; and
R² is hydrogen or $C_1$-$C_{12}$ alkyl.

2. A process of preparing a compound having structural Formula (IIIa):

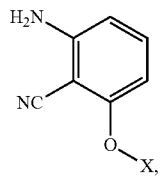

comprising
i) reducing a compound having structural Formula (IV) where R⁴ is nitro to provide the compound having structural Formula (IIIa), or
ii) treating a compound having structural Formula (IV) where R⁴ is halo with ammonia to provide the compound having structural Formula (IIIa),

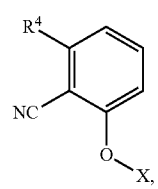

wherein
R⁴ is nitro or halo; and
X is alkyl, substituted alkyl, alkenyl, substituted alkenyl, heteroalkyl, substituted heteroalkyl, heteroalkenyl, or substituted heteroalkenyl.

3. The process of claim 2, comprising reducing the compound having structural Formula (IV) to provide the compound of Formula (IIIa), where R⁴ is nitro.

4. The process of claim 2, comprising treating the compound having structural Formula (IV) with ammonia to provide the compound of Formula (IIIa), where R⁴ is halo.

5. A process of preparing a compound having structural Formula (IIc):

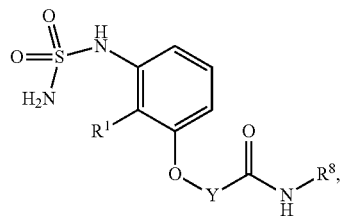

comprising reacting a compound having structural Formula (IX)

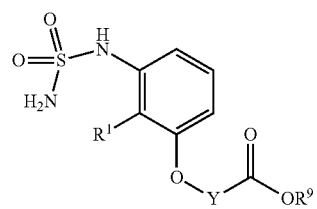

with R⁸—NH₂, in the presence of an activating reagent;
wherein
R¹ is —CN or —C(O)NH₂;
Y is $C_1$-$C_{12}$ alkylene or $C_1$-$C_{12}$ alkenylene;
R⁸ is $C_1$-$C_{12}$ alkyl; and
R⁹ is hydrogen or $C_1$-$C_{12}$ alkyl.

6. A process of preparing a compound having structural Formula (IIc1):

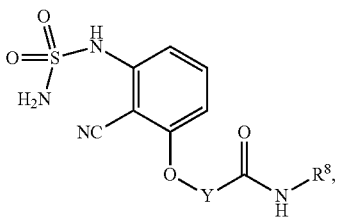

comprising:
adding a solution of a compound having structural Formula (IIIc1)

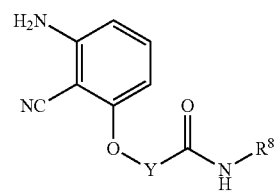

in a mixed solvent of methylene chloride and dimethylacetamide to a solution of Cl—S(O)₂—NH₂ in methylene chloride and optionally an additional solvent to form a mixture;

maintaining the mixture at about room temperature for about 6 to about 18 hours; and extracting the mixture with an aqueous solution of a hydroxide or alkoxide base to form an extracted basic solution wherein the compound having structural formula (IIc1) is stabilized, wherein:

Y is $C_1$-$C_{12}$ alkylene or $C_1$-$C_{12}$ alkenylene; and $R^8$ is $C_1$-$C_{12}$ alkyl.

7. The process of claim 6, wherein the solution is Cl—S(O)$_2$—NH$_2$ in methylene chloride and acetonitrile.

8. A process of preparing a compound having structural Formula (IIc1):

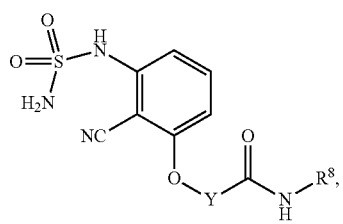

(IIc1)

comprising:

adding a solution of a compound having structural Formula (IIIc1)

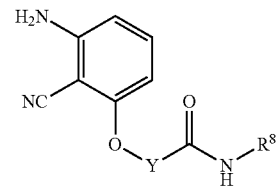

(IIIc1)

in a mixed solvent of methylene chloride and dimethylacetamide to a solution of Cl—S(O)$_2$—NH$_2$ in methylene chloride and optionally an additional solvent to form a first mixture;

maintaining the first mixture at about room temperature for about 6 to about 18 hours;

mixing an aqueous solution of NaHCO$_3$ with the first mixture to form a second mixture, wherein the second mixture is maintained at a temperature of about 45° C. or below during the addition of the aqueous solution of NaHCO$_3$; and extracting the second mixture with an aqueous solution of a hydroxide or alkoxide base to form an extracted basic solution wherein the compound having structural formula (IIc1) is stabilized, wherein:

Y is $C_1$-$C_{12}$ alkylene or $C_1$-$C_{12}$ alkenylene; and $R^8$ is $C_1$-$C_{12}$ alkyl.

9. A process of preparing a compound having structural Formula (IIIc1):

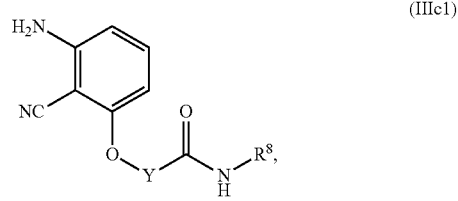

(IIIc1)

comprising reacting HO—Y—C(O)—NHR$^8$ with

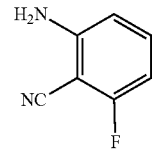

in the presence of a base to form a first mixture solution, concentrating the first mixture solution to form a concentrated first mixture solution, wherein the volume of the concentrated first mixture solution is equivalent to or less than about 50% of the volume of the first mixture solution, diluting the concentrated first mixture solution with an ether to form a second mixture solution and optionally washing the second mixture solution with water or an aqueous solution, concentrating the second mixture solution to form a concentrated second mixture solution, wherein the volume of the concentrated second mixture solution is equivalent to or less than about 50% of the volume of the second mixture solution, diluting the concentrated second mixture solution with ethyl acetate to form a third mixture solution, and concentrating the third mixture solution to form a concentrated third mixture solution, wherein the compound having structural Formula (IIIc1) precipitates as a solid and optionally diluting the concentrated third mixture solution with an alkane hydrocarbon solvent;

wherein

Y is $C_1$-$C_{12}$ alkylene; and $R^8$ is $C_1$-$C_{12}$ alkyl.

10. The process of claim 9 comprising diluting the concentrated third mixture solution with an alkane hydrocarbon solvent.

11. The process of claim 9 comprising washing the second mixture solution with water or an aqueous solution.

* * * * *